US010266813B2

(12) United States Patent
Ayer et al.

(10) Patent No.: US 10,266,813 B2
(45) Date of Patent: Apr. 23, 2019

(54) EXONUCLEASE DEFICIENT POLYMERASES

(71) Applicant: Genia Technologies, Inc., Santa Clara, CA (US)

(72) Inventors: Aruna Ayer, Santa Clara, CA (US); Arkadiusz Bibillo, Cupertino, CA (US); Preethi Sarvabhowman, Santa Clara, CA (US); Dhruti Vasudev Dalal, Sunnyvale, CA (US); Ilya Lederman, San Francisco, CA (US); Eileen Thai, San Jose, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/444,020

(22) Filed: Feb. 27, 2017

(65) Prior Publication Data

US 2017/0267983 A1 Sep. 21, 2017

Related U.S. Application Data

(60) Provisional application No. 62/301,475, filed on Feb. 29, 2016.

(51) Int. Cl.
*C12N 9/12* (2006.01)
*C12N 15/00* (2006.01)
*C07H 21/04* (2006.01)

(52) U.S. Cl.
CPC .... *C12N 9/1252* (2013.01); *C12Y 207/07007* (2013.01)

(58) Field of Classification Search
None
See application file for complete search history.

(56) References Cited

U.S. PATENT DOCUMENTS

| 4,683,202 | A | 7/1987 | Mullis |
| 9,266,109 | B2 | 2/2016 | Howell et al. |
| 2010/0035254 | A1 | 2/2010 | Williams |
| 2012/0071359 | A1 | 3/2012 | Sun |
| 2012/0322666 | A1 | 12/2012 | Pham et al. |
| 2013/0053544 | A1 | 2/2013 | Howarth |
| 2014/0113291 | A1 | 4/2014 | Bernick et al. |
| 2014/0134616 | A1 | 5/2014 | Davis et al. |
| 2015/0167072 | A1 | 6/2015 | Sun et al. |
| 2015/0368626 | A1 | 12/2015 | Vander Horn et al. |
| 2016/0222363 | A1 | 8/2016 | Ayer et al. |
| 2016/0267983 | A1 | 9/2016 | Bushnaq et al. |
| 2016/0333327 | A1 | 11/2016 | Ayer et al. |

FOREIGN PATENT DOCUMENTS

| WO | 2006028508 | A2 | 3/2006 |
| WO | 2011097028 | A1 | 8/2011 |
| WO | 2012083249 | A2 | 6/2012 |
| WO | 2012129242 | A2 | 9/2012 |
| WO | 2013188841 | A1 | 12/2013 |
| WO | 2014074727 | A1 | 5/2014 |
| WO | 2015061510 | A1 | 4/2015 |
| WO | 2015061511 | A1 | 4/2015 |
| WO | 2016124543 | A1 | 8/2016 |
| WO | 2016183403 | A2 | 11/2016 |
| WO | 2017148861 | A1 | 9/2017 |
| WO | 2017148862 | A1 | 9/2017 |

OTHER PUBLICATIONS

AFH27088, PUBMED, 2012, retrieved from the Internet at http://www.ebi.ac.uk/ena/data/view/AFH270888&display=text.
AFH27143, PUBMED, 2012, retrieved from the Internet: http://www.ebi.ac.uk/ena/data/view/AFH27143&display=text.
Altschul et al, Basic Local Alignment Search Tool, Journal of Molecular Biology, 1990, pp. 403-410, vol. 215.
Altschul, Stephen F. et al., Gapped BLAST and PSI-BLAST: a new generation of protein database search programs, Nucleic Acids Research, 1997, pp. 3389-3402, vol. 25, No. 17.
Gardner et al, 2012, "Rapid incorporation kinetics and improved fidelity of a novel class of 3'-OH unblocked reversible terminators", Nucleic Acids Research, 140(15):7404-7415.
Johnson, Kenneth A., 2010,"The kinetic and chemical mechanism of high-fidelity DNA polymerases", Biochimica et Biophysica Acta, 1804:1041-1048.
Kong et al, 1993, "Characterization of a DNA Polymerase form the Hyperthermophile Archaea Thermococcus litoralist", The Journal of Biological Chemistry, 268(3):1965-1975.
Kranaster et al, 2009, "Taking Fingerprints of DNA Polymerases: Multiplex Enzyme Profiling on DNA Arrays", Angewandte Chemie International Edition, 48(25):4625-4628.
Lawyer et al, Isolation, 1989, "Characterization, and Expression in *Escherichia coli* of the DNA Polymerase Gene from Thermus aquaticus", The Journal of Biological Chemistry, 264(11):6427-6437.
Li et al, 2014, "Structural Analysis and Optimization of the Covalent Association between SpyCatcher and a Peptide Tag", Journal of Molecular Biology, 426:309-317.
Volozhanstsev, et al., UniProt Submission 13PV37 9CAUD (Apr. 1, 2015) (Retrieved from the Internet Aug. 18, 2016).
Volozhantsev, et al. Molecular Characterization of Podoviral Bacteriophages Virulent for Clostridium perfringens and Their Comparison with Members of the Picovirinae. PloS ONE 2012, 7:e38283-e38283.
Written Opinion for PCT/EP2016/052068, dated Jan. 2, 2016.
Written Opinion for PCT/US2016/032258, dated Aug. 21, 2016.
Written Opinion for PCT/EP2017/054502, dated May 3, 2017.

(Continued)

*Primary Examiner* — Yong D Pak
(74) *Attorney, Agent, or Firm* — Roche Molecular Systems, Inc.

(57) ABSTRACT

Described herein are polymerase variants that are exonuclease deficient. Some variants retain the strand displacement capability comparable to the wild-type or parental polymerase. Some variants have a strand displacement capability that is improved relative to the wild-type or parental polymerase. The variants may have an extension rate that is greater than the wild-type or parental polymerase. The variants may have a waiting time that is less than the wild-type or parental polymerase.

15 Claims, 5 Drawing Sheets

Specification includes a Sequence Listing.

(56) References Cited

OTHER PUBLICATIONS

Written Opinion for PCT/EP2017/054501, dated May 3, 2017.
Zakeri et al, 2010, "Spontaneous Intermolecular Amide Bond Formation between Side Chains for Irreversible Peptide Targeting", Journal of the American Chemical Society, 132:4526-4527.
Zakeri et al, 2012, "Peptide tag forming a rapid covalent bond to a protein, through engineering a bacterial adhesion", PNAS, 109(12):E690-E697 w/supporting figs (19 pp.).
Astier et al, Toward Single Molecule DNA Sequencing: Direct Identification of Ribonucleoside and Deoxyribonucleoside 5'-Monophosphates by Using an Engineered Protein Nanopore Equipped with a Molecular Adapter, Journal of the American Chemical Society, Dec. 30, 2005, Published online Dec. 30, 2005 at https://pdfs.semanticscholar.org/8d63/1eba6e52b49f99729640dcdced07f1263ebb.pdf, 10.1021/ja057123+.
Ausubel et al, Short Protocols in Molecular Biology, Current Protocols in Molecular Biology, 1992, Table of Contents, Second Edition, Greene Publishing Associates & John Wiley & Sons.
Ausubel, F.M. et al., Current Protocols in Molecular Biology, Wiley & Sons Inc., 1987-1994, 1.
Dennler et al, Transglutaminase-Based Chemo-Enzymatic Conjugation Approach Yields Homogeneous Antibody-Drug Conjugates, Bioconjugate Chemistry, 2014, pp. 569-578, vol. 25.
Hale et al, HarperCollins Dictionary of Biology, CarperCollins Dictionary of Biology, 1991, Cover, Synopsis from AbeBooks, (none).
Heck et al, Enzyme-catalyzed protein crosslinking, Appl Microbiol Biotechnol, 2013, pp. 461-475, vol. 97.
Horhota et al, Glycerol Nucleoside Triphosphates: Synthesis and Polymerase Substrate, Organic Letters, 2006, pp. 5345-5347, vol. 8, No. 23.
Kranaster et al, One-step RNA pathogen detection with reverse transcriptase activity of a mutated thermostable Thermus aquaticus DNA polymerase, Biotechnology Journal, 2010, pp. 224-231, vol. 5, Issue 2.
Rashidian, Mohammad et al., Enzymatic Labeling of Proteins: Techniques and Approaches, Bioconjugate Chemistry, 2013, pp. 1277-1294, vol. 24.
Saiki et al, Primer-Directed Enzymatic Amplification of DNA with a thermostable DNA polymerase, Science, Jan. 29, 2988, pp. 487-491, vol. 239, No. 4839.
Sambrook et al, Chapter 9: Preparation of Radiolabeled DNA and RNA Probes, Chapter 9: Molecular Cloning: A Laboratory Manual, 2001, Sections 9.63-9.75, vol. 2, Third Edition, Cold Spring Harbor Laboratory Press.
Sambrook et al, Molecular Cloning a Laboratory Manual, Molecular Cloning: a Laboratory Manual, 1989, Cover, Bibliography, Table of Contents, Third Edition, Cold Spring Harbor Laboratory Press.
Singleton et al, Dictionary of Microbiology and Molecular Biology, Dictionary of Microbiology and Molecular Biology, Second Edition, 1987, Cover, Bibliography, Preface, Table of Contents, Note for the User, Second Edition, John Wiley and Sons.
Singleton et al, Dictionary of Microbiology and Molecular Biology, Dictionary of Microbiology and Molecular Biology, Second Edition, 1994, Cover, Second Edition, John Wiley and Sons, NY.
Thapa et al, Native Chemical Ligation: A Boon to Peptide Chemistry, Molecules, 2014, pp. 14461-14483, vol. 19.
Volozhantsev et al, AFH27113 Clostridium phage phiCPV4 DNA polymerase, Pubmed, May 28, 2012, 3 pages.
Watson et al, Molecular Biology of the Gene, Molecular Biology of the Gene, 1987, Cover, Bibliography, Preface, Reviewers, Brief Contents, Detailed Contents, Fourth Edition, The Benjamin/Cummings Publishing Company, Inc., Menlo Park.
Wu et al, Sortase-Mediated Transpeptidation for Site-Specific Modification of Peptides, Glycopeptides, and Proteins, J Carbohyd Chem., 2012, pp. 48-66, vol. 31, No. 1.
Eid, J, et al., Real-Time DNA Sequencing from single Polymerase Molecules, Science, vol. 323, pp. 133-138 (2009).
Fiss, E.H. et al., DNA polymerases with improved reverse transcriptase activity, FASEB J, (2009), 482.4 / retrieved from the internet: http://www.fasebj.org/doi/abs/10.1096/fasebj.23.1_supplement.482.4, vol. 23 No. 1 Suppl.
Fuller, C. et al, Real-time single-molecule electronic DNA sequencing by synthesis using polymer-tagged nucleotides on a nanopore array, PNAS, (2016), pp. 5233-5238, vol. 113, No. 19.
International Search Report and Written Opinion dated Jul. 7, 2017 in corresponding PCT/EP2017/054500 filed on Feb. 27, 2017, pp. 1-20.
Kumar et al, PEG-Labeled Nucleotides and Nanopore Detection for Single Molecule DNA Sequencing by Synthesis, Scientific Reports, 2012, pp. 1-8, vol. 2.
Ngo et al, Computational Complexity, Protein Structure Prediction, and the Levinthal Paradox, The Protein Folding Problem and Tertiary Structure Prediction, 1994, pp. 433, 492-495, unknown, Merz & Le Grand.
UniProt Submission 13PV37 9CAUD (Apr. 1, 2015) (Retrieved from the Internet Aug. 18, 2016).

SEQUENCE LISTING

```
<160> NUMBER OF SEQ ID NOS: 14

<210> SEQ ID NO 1
<211> LENGTH: 727
<212> TYPE: PRT
<213> ORGANISM: Clostridium phage phiCPV4

<400> SEQUENCE: 1

Met Asp Lys His Thr Gln Tyr Val Lys Glu His Ser Phe Asn Tyr Asp
1               5                   10                  15

Glu Tyr Lys Lys Ala Asn Phe Asp Lys Ile Glu Cys Leu Ile Phe Asp
            20                  25                  30

Thr Glu Ser Cys Thr Asn Tyr Glu Asn Asp Asn Thr Gly Ala Arg Val
        35                  40                  45

Tyr Gly Trp Gly Leu Gly Val Thr Arg Asn His Asn Met Ile Tyr Gly
    50                  55                  60

Gln Asn Leu Asn Gln Phe Trp Glu Val Cys Gln Asn Ile Phe Asn Asp
65                  70                  75                  80

Trp Tyr His Asp Asn Lys His Thr Ile Lys Ile Thr Lys Thr Lys Lys
                85                  90                  95

Gly Phe Pro Lys Arg Lys Tyr Ile Lys Phe Pro Ile Ala Val His Asn
            100                 105                 110

Leu Gly Trp Asp Val Glu Phe Leu Lys Tyr Ser Leu Val Glu Asn Gly
        115                 120                 125

Phe Asn Tyr Asp Lys Gly Leu Leu Lys Thr Val Phe Ser Lys Gly Ala
    130                 135                 140

Pro Tyr Gln Thr Val Thr Asp Val Glu Glu Pro Lys Thr Phe His Ile
145                 150                 155                 160

Val Gln Asn Asn Asn Ile Val Tyr Gly Cys Asn Val Tyr Met Asp Lys
                165                 170                 175

Phe Phe Glu Val Glu Asn Lys Asp Gly Ser Thr Thr Glu Ile Gly Leu
            180                 185                 190

Cys Leu Asp Phe Phe Asp Ser Tyr Lys Ile Ile Thr Cys Ala Glu Ser
        195                 200                 205

Gln Phe His Asn Tyr Val His Asp Val Asp Pro Met Phe Tyr Lys Met
    210                 215                 220

Gly Glu Glu Tyr Asp Tyr Asp Thr Trp Arg Ser Pro Thr His Lys Gln
225                 230                 235                 240

Thr Thr Leu Glu Leu Arg Tyr Gln Tyr Asn Asp Ile Tyr Met Leu Arg
                245                 250                 255

Glu Val Ile Glu Gln Phe Tyr Ile Asp Gly Leu Cys Gly Gly Glu Leu
            260                 265                 270

Pro Leu Thr Gly Met Arg Thr Ala Ser Ser Ile Ala Phe Asn Val Leu
        275                 280                 285
```

```
Lys Lys Met Thr Phe Gly Glu Glu Lys Thr Glu Gly Tyr Ile Asn
        290                 295                 300

Tyr Phe Glu Leu Asp Lys Lys Thr Lys Phe Glu Phe Leu Arg Lys Arg
305                 310                 315                 320

Ile Glu Met Glu Ser Tyr Thr Gly Gly Tyr Thr His Ala Asn His Lys
                325                 330                 335

Ala Val Gly Lys Thr Ile Asn Lys Ile Gly Cys Ser Leu Asp Ile Asn
            340                 345                 350

Ser Ser Tyr Pro Ser Gln Met Ala Tyr Lys Val Phe Pro Tyr Gly Lys
        355                 360                 365

Pro Val Arg Lys Thr Trp Gly Arg Lys Pro Lys Thr Glu Lys Asn Glu
370                 375                 380

Val Tyr Leu Ile Glu Val Gly Phe Asp Phe Val Glu Pro Lys His Glu
385                 390                 395                 400

Glu Tyr Ala Leu Asp Ile Phe Lys Ile Gly Ala Val Asn Ser Lys Ala
                405                 410                 415

Leu Ser Pro Ile Thr Gly Ala Val Ser Gly Gln Glu Tyr Phe Cys Thr
            420                 425                 430

Asn Ile Lys Asp Gly Lys Ala Ile Pro Val Tyr Lys Glu Leu Lys Asp
        435                 440                 445

Thr Lys Leu Thr Thr Asn Tyr Asn Val Val Leu Thr Ser Val Glu Tyr
450                 455                 460

Glu Phe Trp Ile Lys His Phe Asn Phe Gly Val Phe Lys Lys Asp Glu
465                 470                 475                 480

Tyr Asp Cys Phe Glu Val Asp Asn Leu Glu Phe Thr Gly Leu Lys Ile
                485                 490                 495

Gly Ser Ile Leu Tyr Tyr Lys Ala Glu Lys Gly Lys Phe Lys Pro Tyr
            500                 505                 510

Val Asp His Phe Thr Lys Met Lys Val Glu Asn Lys Lys Leu Gly Asn
        515                 520                 525

Lys Pro Leu Thr Asn Gln Ala Lys Leu Ile Leu Asn Gly Ala Tyr Gly
        530                 535                 540

Lys Phe Gly Thr Lys Gln Asn Lys Glu Glu Lys Asp Leu Ile Met Asp
545                 550                 555                 560

Lys Asn Gly Leu Leu Thr Phe Thr Gly Ser Val Thr Glu Tyr Glu Gly
                565                 570                 575

Lys Glu Phe Tyr Arg Pro Tyr Ala Ser Phe Val Thr Ala Tyr Gly Arg
            580                 585                 590

Leu Gln Leu Trp Asn Ala Ile Ile Tyr Ala Val Gly Val Glu Asn Phe
        595                 600                 605

Leu Tyr Cys Asp Thr Asp Ser Ile Tyr Cys Asn Arg Glu Val Asn Ser
        610                 615                 620

Leu Ile Glu Asp Met Asn Ala Ile Gly Glu Thr Ile Asp Lys Thr Ile
625                 630                 635                 640

Leu Gly Lys Trp Asp Val Glu His Val Phe Asp Lys Phe Lys Val Leu
                645                 650                 655

Gly Gln Lys Lys Tyr Met Tyr His Asp Cys Lys Glu Asp Lys Thr Asp
            660                 665                 670

Leu Lys Cys Cys Gly Leu Pro Ser Asp Ala Arg Lys Ile Ile Ile Gly
        675                 680                 685

Gln Gly Phe Asp Glu Phe Tyr Leu Gly Lys Asn Val Glu Gly Lys Lys
        690                 695                 700
```

```
Gln Arg Lys Lys Val Ile Gly Gly Cys Leu Leu Leu Asp Thr Leu Phe
705                 710                 715                 720

Thr Ile Lys Lys Ile Met Phe
                725
```

<210> SEQ ID NO 2
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met His His His His His His Ser Gly Gly Ser Asp Lys His
1               5                   10                  15

Thr Gln Tyr Val Lys Glu His Ser Phe Asn Tyr Asp Glu Tyr Lys Lys
            20                  25                  30

Ala Asn Phe Asp Lys Ile Glu Cys Leu Ile Phe Asp Thr Glu Ser Cys
        35                  40                  45

Thr Asn Tyr Glu Asn Asp Asn Thr Gly Ala Arg Val Tyr Gly Trp Gly
    50                  55                  60

Leu Gly Val Thr Arg Asn His Asn Met Ile Tyr Gly Gln Asn Leu Asn
65                  70                  75                  80

Gln Phe Trp Glu Val Cys Gln Asn Ile Phe Asn Asp Trp Tyr His Asp
                85                  90                  95

Asn Lys His Thr Ile Lys Ile Thr Lys Thr Lys Lys Gly Phe Pro Lys
            100                 105                 110

Arg Lys Tyr Ile Lys Phe Pro Ile Ala Val His Asn Leu Gly Trp Asp
        115                 120                 125

Val Glu Phe Leu Lys Tyr Ser Leu Val Glu Asn Gly Phe Asn Tyr Asp
    130                 135                 140

Lys Gly Leu Leu Lys Thr Val Phe Ser Lys Gly Ala Pro Tyr Gln Thr
145                 150                 155                 160

Val Thr Asp Val Glu Glu Pro Lys Thr Phe His Ile Val Gln Asn Asn
                165                 170                 175

Asn Ile Val Tyr Gly Cys Asn Val Tyr Met Asp Lys Phe Phe Glu Val
            180                 185                 190

Glu Asn Lys Asp Gly Ser Thr Thr Glu Ile Gly Leu Cys Leu Asp Phe
        195                 200                 205

Phe Asp Ser Tyr Lys Ile Ile Thr Cys Ala Glu Ser Gln Phe His Asn
    210                 215                 220

Tyr Val His Asp Val Asp Pro Met Phe Tyr Lys Met Gly Glu Glu Tyr
225                 230                 235                 240

Asp Tyr Asp Thr Trp Arg Ser Pro Thr His Lys Gln Thr Thr Leu Glu
                245                 250                 255

Leu Arg Tyr Gln Tyr Asn Asp Ile Tyr Met Leu Arg Glu Val Ile Glu
            260                 265                 270

Gln Phe Tyr Ile Asp Gly Leu Cys Gly Gly Glu Leu Pro Leu Thr Gly
        275                 280                 285

Met Arg Thr Ala Ser Ser Ile Ala Phe Asn Val Leu Lys Lys Met Thr
    290                 295                 300

Phe Gly Glu Glu Lys Thr Glu Glu Gly Tyr Ile Asn Tyr Phe Glu Leu
305                 310                 315                 320

Asp Lys Lys Thr Lys Phe Glu Phe Leu Arg Lys Arg Ile Glu Met Glu
                325                 330                 335
```

-continued

```
Ser Tyr Thr Gly Gly Tyr Thr His Ala Asn His Lys Ala Val Gly Lys
            340                 345                 350

Thr Ile Asn Lys Ile Gly Cys Ser Leu Asp Ile Asn Ser Ser Tyr Pro
355                 360                 365

Ser Gln Met Ala Tyr Lys Val Phe Pro Tyr Gly Lys Pro Val Arg Lys
    370                 375                 380

Thr Trp Gly Arg Lys Pro Lys Thr Glu Lys Asn Glu Val Tyr Leu Ile
385                 390                 395                 400

Glu Val Gly Phe Asp Phe Val Glu Pro Lys His Glu Glu Tyr Ala Leu
                405                 410                 415

Asp Ile Phe Lys Ile Gly Ala Val Asn Ser Lys Ala Leu Ser Pro Ile
            420                 425                 430

Thr Gly Ala Val Ser Gly Gln Glu Tyr Phe Cys Thr Asn Ile Lys Asp
            435                 440                 445

Gly Lys Ala Ile Pro Val Tyr Lys Glu Leu Lys Asp Thr Lys Leu Thr
    450                 455                 460

Thr Asn Tyr Asn Val Val Leu Thr Ser Val Glu Tyr Glu Phe Trp Ile
465                 470                 475                 480

Lys His Phe Asn Phe Gly Val Phe Lys Lys Asp Glu Tyr Asp Cys Phe
                485                 490                 495

Glu Val Asp Asn Leu Glu Phe Thr Gly Leu Lys Ile Gly Ser Ile Leu
            500                 505                 510

Tyr Tyr Lys Ala Glu Lys Gly Lys Phe Lys Pro Tyr Val Asp His Phe
            515                 520                 525

Thr Lys Met Lys Val Glu Asn Lys Lys Leu Gly Asn Lys Pro Leu Thr
            530                 535                 540

Asn Gln Ala Lys Leu Ile Leu Asn Gly Ala Tyr Gly Lys Phe Gly Thr
545                 550                 555                 560

Lys Gln Asn Lys Glu Glu Lys Asp Leu Ile Met Asp Lys Asn Gly Leu
                565                 570                 575

Leu Thr Phe Thr Gly Ser Val Thr Glu Tyr Glu Gly Lys Glu Phe Tyr
            580                 585                 590

Arg Pro Tyr Ala Ser Phe Val Thr Ala Tyr Gly Arg Leu Gln Leu Trp
            595                 600                 605

Asn Ala Ile Ile Tyr Ala Val Gly Val Glu Asn Phe Leu Tyr Cys Asp
610                 615                 620

Thr Asp Ser Ile Tyr Cys Asn Arg Glu Val Asn Ser Leu Ile Glu Asp
625                 630                 635                 640

Met Asn Ala Ile Gly Glu Thr Ile Asp Lys Thr Ile Leu Gly Lys Trp
                645                 650                 655

Asp Val Glu His Val Phe Asp Lys Phe Lys Val Leu Gly Gln Lys Lys
            660                 665                 670

Tyr Met Tyr His Asp Cys Lys Glu Asp Lys Thr Asp Leu Lys Cys Cys
            675                 680                 685

Gly Leu Pro Ser Asp Ala Arg Lys Ile Ile Gly Gln Gly Phe Asp
    690                 695                 700

Glu Phe Tyr Leu Gly Lys Asn Val Glu Gly Lys Lys Gln Arg Lys Lys
705                 710                 715                 720

Val Ile Gly Gly Cys Leu Leu Leu Asp Thr Leu Phe Thr Ile Lys Lys
                725                 730                 735

Ile Met Phe
```

<210> SEQ ID NO 3
<211> LENGTH: 2220
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | | | | | |
|---|---|---|---|---|---|
| atgcatcacc | atcatcatca | ccaccacagc | ggcggttccg | acaaacacac | gcagtacgtc | 60 |
| aaagagcata | gcttcaatta | tgacgagtat | aagaaagcga | atttcgacaa | gatcgagtgc | 120 |
| ctgatctttg | acaccgagag | ctgcacgaat | atgagaacg | ataataccgg | tgcacgtgtt | 180 |
| tacggttggg | gtcttggcgt | cacccgcaac | cacaatatga | tctacggcca | aaatctgaat | 240 |
| cagttttggg | aagtatgcca | gaacatttc | aatgattggt | atcacgacaa | caaacatacc | 300 |
| attaagatta | ccaagaccaa | gaaaggcttc | ccgaaacgta | agtacattaa | gtttccgatt | 360 |
| gcagttcaca | atttgggctg | ggatgttgaa | ttcctgaagt | atagcctggt | ggagaatggt | 420 |
| ttcaattacg | acaagggtct | gctgaaaact | gttttagca | agggtgcgcc | gtaccaaacc | 480 |
| gtgaccgatg | ttgaggaacc | gaaaacgttc | catatcgtcc | agaataacaa | catcgtttat | 540 |
| ggttgtaacg | tgtatatgga | caaattcttt | gaggtcgaga | caaagacgg | ctctaccacc | 600 |
| gagattggcc | tgtgcttgga | tttcttcgat | agctataaga | tcatcacgtg | tgctgagagc | 660 |
| cagttccaca | attacgttca | tgatgtggat | ccaatgttct | acaaaatggg | tgaagagtat | 720 |
| gattacgata | cttggcgtag | cccgacgcac | aagcagacca | ccctggagct | gcgctaccaa | 780 |
| tacaatgata | tctatatgct | gcgtgaagtc | atcgaacagt | tttacattga | cggtttatgt | 840 |
| ggcggcgagc | tgccgctgac | cggcatgcgc | accgcttcca | gcattgcgtt | caacgtgctg | 900 |
| aaaaagatga | cctttggtga | ggaaaagacg | gaagagggct | acatcaacta | ttttgaattg | 960 |
| gacaagaaaa | ccaaattcga | gtttctgcgt | aagcgcattg | aaatggaatc | gtacaccggt | 1020 |
| ggctatacgc | acgcaaatca | caagccgtt | ggtaagacta | ttaacaagat | cggttgctct | 1080 |
| ttggacatta | acagctcata | ccctccgcag | atggcgtaca | aggtctttcc | gtatggcaaa | 1140 |
| ccggttcgta | agacctgggg | tcgtaaacca | aagaccgaga | gaacgaagt | ttatctgatt | 1200 |
| gaagttggct | ttgacttcgt | ggagccgaaa | cacgaagaat | acgcgctgga | tatctttaag | 1260 |
| attggtgcgg | tgaactctaa | agcgctgagc | ccgatcaccg | cgctgtcag | cggtcaagag | 1320 |
| tatttctgta | cgaacattaa | agacggcaaa | gcaatcccgg | tttacaaaga | actgaaggac | 1380 |
| accaaattga | ccactaacta | caatgtcgtg | ctgaccagcg | tggagtacga | gttctggatc | 1440 |
| aaacacttca | attttggtgt | gtttaagaaa | gacgagtacg | actgtttcga | agttgacaat | 1500 |
| ctggagttta | cgggtctgaa | gattggttcc | attctgtact | acaaggcaga | gaaaggcaag | 1560 |
| tttaaacctt | acgtggatca | cttcacgaaa | atgaaagtgg | agaacaagaa | actgggtaat | 1620 |
| aagccgctga | cgaatcaggc | aaagctgatt | ctgaacggtg | cgtacggcaa | attcggcacc | 1680 |
| aaacaaaaca | aagaagagaa | agatttgatc | atggataaga | acggtttgct | gaccttcacg | 1740 |
| ggtagcgtca | cggaatacga | gggtaaagaa | ttctatcgtc | cgtatgcgag | cttcgttact | 1800 |
| gcctatggtc | gcctgcaact | gtggaacgcg | attatctacg | cggttggtgt | ggagaatttt | 1860 |
| ctgtactgcg | acaccgacag | catctattgt | aaccgtgaag | ttaacagcct | cattgaggat | 1920 |
| atgaacgcca | ttggtgaaac | catcgataaa | acgattctgg | gtaaatggga | cgtggagcat | 1980 |
| gtctttgata | agtttaaggt | cctgggccag | aagaagtaca | tgtatcatga | ttgcaaagaa | 2040 |
| gataaaacgg | acctgaagtg | ttgcggtctg | ccgagccgatg | cccgtaagat | tatcattggt | 2100 |

```
caaggtttcg acgagtttta tctgggcaaa aatgtcgaag gtaagaagca acgcaaaaaa    2160
gtgatcggcg gttgcctgct gctggacacc ctgtttacga tcaagaaaat catgttctaa   2220
```

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
agagtgatag tatgattatg tagatgtagg atttgatatg tgagtagccg aatgaaacct    60
t                                                                   61
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
ttttcataat catactatca ctct                                           24
```

<210> SEQ ID NO 6
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
agagtgatag tatgattatg tagatgtagg atttgatatg tgagtagccg aatgaaacct    60
ttggtttcat tcgg                                                     74
```

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ttttcatatc aaatcctaca tctacataat catactatca ctct                    44
```

<210> SEQ ID NO 8
<211> LENGTH: 727
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Asp Lys His Thr Gln Tyr Val Lys Glu His Ser Phe Asn Tyr Asp
1               5                   10                  15

Glu Tyr Lys Lys Ala Asn Phe Asp Lys Ile Glu Cys Leu Ile Phe Asp
            20                  25                  30

Thr Glu Ser Cys Thr Asn Tyr Glu Asn Asp Asn Thr Gly Ala Arg Val
```

```
                35                  40                  45
Tyr Gly Trp Gly Leu Gly Val Thr Arg Asn His Asn Met Ile Tyr Gly
 50                  55                  60

Gln Asn Leu Asn Gln Phe Trp Glu Val Cys Gln Asn Ile Phe Asn Asp
 65                  70                  75                  80

Trp Tyr His Asp Asn Lys His Thr Ile Lys Ile Thr Lys Thr Lys Lys
                 85                  90                  95

Gly Phe Pro Lys Arg Lys Tyr Ile Lys Phe Pro Ile Ala Val His Asn
                100                 105                 110

Leu Gly Trp Asp Val Glu Phe Leu Lys Tyr Ser Leu Val Glu Asn Gly
                115                 120                 125

Phe Asn Tyr Asp Lys Gly Leu Leu Lys Thr Val Phe Ser Lys Gly Ala
130                 135                 140

Pro Tyr Gln Thr Val Thr Asp Val Glu Pro Lys Thr Phe His Ile
145                 150                 155                 160

Val Gln Asn Asn Ile Val Tyr Gly Cys Asn Val Tyr Met Asp Lys
                165                 170                 175

Phe Phe Glu Val Glu Asn Lys Asp Gly Ser Thr Thr Glu Ile Gly Leu
                180                 185                 190

Cys Leu Asp Phe Phe Asp Ser Tyr Lys Ile Ile Thr Cys Ala Glu Ser
                195                 200                 205

Gln Phe His Asn Tyr Val His Asp Val Asp Pro Met Phe Tyr Lys Met
210                 215                 220

Gly Glu Glu Tyr Asp Tyr Asp Thr Trp Arg Ser Pro Thr His Lys Gln
225                 230                 235                 240

Thr Thr Leu Glu Leu Arg Tyr Gln Tyr Asn Asp Ile Tyr Met Leu Arg
                245                 250                 255

Glu Val Ile Glu Gln Phe Tyr Ile Asp Gly Leu Cys Gly Gly Glu Leu
                260                 265                 270

Pro Leu Thr Gly Met Arg Thr Ala Ser Ser Ile Ala Phe Asn Val Leu
                275                 280                 285

Lys Lys Met Thr Phe Gly Glu Glu Lys Thr Glu Glu Gly Tyr Ile Asn
                290                 295                 300

Tyr Phe Glu Leu Asp Lys Lys Thr Lys Phe Glu Phe Leu Arg Lys Arg
305                 310                 315                 320

Ile Glu Met Glu Ser Tyr Thr Gly Gly Tyr Thr His Ala Asn His Lys
                325                 330                 335

Ala Val Gly Lys Thr Ile Asn Lys Ile Gly Cys Ser Leu Asp Ile Asn
                340                 345                 350

Ser Ala Tyr Pro Ser Gln Met Ala Tyr Lys Val Phe Pro Tyr Gly Lys
                355                 360                 365

Pro Val Arg Lys Thr Trp Gly Arg Lys Pro Lys Thr Glu Lys Asn Glu
370                 375                 380

Val Tyr Leu Ile Glu Val Gly Phe Asp Phe Val Glu Pro Lys His Glu
385                 390                 395                 400

Glu Tyr Ala Leu Asp Ile Phe Lys Ile Gly Ala Val Asn Ser Lys Ala
                405                 410                 415

Leu Ser Pro Ile Thr Gly Ala Val Ser Gly Gln Glu Tyr Phe Cys Thr
                420                 425                 430

Asn Ile Lys Asp Gly Lys Ala Ile Pro Val Tyr Lys Glu Leu Lys Asp
                435                 440                 445

Thr Lys Leu Thr Thr Asn Tyr Asn Val Val Leu Thr Ser Val Glu Tyr
450                 455                 460
```

-continued

```
Glu Phe Trp Ile Lys His Phe Asn Phe Gly Val Phe Lys Lys Asp Glu
465                 470                 475                 480

Tyr Asp Cys Phe Glu Val Asp Asn Leu Glu Phe Thr Gly Leu Lys Ile
            485                 490                 495

Gly Ser Ile Leu Tyr Tyr Lys Ala Glu Lys Gly Lys Phe Lys Pro Tyr
        500                 505                 510

Val Asp His Phe Met Lys Met Lys Val Glu Asn Lys Lys Leu Gly Asn
    515                 520                 525

Lys Pro Leu Thr Asn Gln Phe Lys Leu Ile Leu Asn Gly Ala Tyr Gly
530                 535                 540

Lys Phe Gly Thr Lys Gln Asn Lys Glu Glu Lys Asp Leu Ile Met Asp
545                 550                 555                 560

Lys Asn Gly Leu Leu Thr Phe Thr Gly Ser Val Thr Glu Tyr Glu Gly
                565                 570                 575

Lys Glu Phe Tyr Arg Pro Tyr Ala Ser Phe Val Thr Ala Tyr Gly Arg
            580                 585                 590

Leu Gln Leu Trp Asn Ala Ile Ile Tyr Ala Val Gly Val Glu Asn Phe
        595                 600                 605

Leu Tyr Cys Asp Thr Asp Ser Ile Tyr Cys Asn Arg Glu Val Asn Ser
    610                 615                 620

Leu Ile Glu Asp Met Asn Ala Ile Gly Glu Thr Ile Asp Lys Thr Ile
625                 630                 635                 640

Leu Gly Lys Trp Asp Val His Val Phe Asp Lys Phe Lys Val Leu
                645                 650                 655

Gly Gln Lys Lys Tyr Met Tyr His Asp Cys Lys Glu Asp Lys Thr Asp
            660                 665                 670

Leu Lys Cys Cys Gly Leu Pro Ser Asp Ala Arg Lys Ile Ile Gly
        675                 680                 685

Gln Gly Phe Asp Glu Phe Tyr Leu Gly Lys Asn Val Glu Gly Lys Lys
690                 695                 700

Gln Arg Lys Lys Val Ile Gly Gly Cys Leu Leu Leu Asp Thr Leu Phe
705                 710                 715                 720

Thr Ile Lys Lys Ile Met Phe
            725
```

<210> SEQ ID NO 9
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
cgctcacact cgctctctct acgtcactca tctcactact gcactctact cgacactcta    60
ctacagctag ctctctctac gacgcacatc acgctactac actctgctct acactacact   120
ctctctacat cgctctacta cgctcatcta                                    150

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtgtgagcgt agatgagc						18

<210> SEQ ID NO 11
<211> LENGTH: 727
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Lys His Thr Gln Tyr Val Lys Glu His Ser Phe Asn Tyr Asp
1               5                   10                  15

Glu Tyr Lys Lys Ala Asn Phe Asp Lys Ile Glu Cys Leu Ile Phe Ala
            20                  25                  30

Thr Glu Ser Cys Thr Asn Tyr Glu Asn Asp Asn Thr Gly Ala Arg Val
        35                  40                  45

Tyr Gly Trp Gly Leu Gly Val Thr Arg Asn His Asn Met Ile Tyr Gly
    50                  55                  60

Gln Asn Leu Asn Gln Phe Trp Glu Val Cys Gln Asn Ile Phe Asn Asp
65                  70                  75                  80

Trp Tyr His Asp Asn Lys His Thr Ile Lys Ile Thr Lys Thr Lys Lys
                85                  90                  95

Gly Phe Pro Lys Arg Lys Tyr Ile Lys Phe Pro Ile Ala Val His Asn
            100                 105                 110

Leu Gly Trp Asp Val Glu Phe Leu Lys Tyr Ser Leu Val Glu Asn Gly
        115                 120                 125

Phe Asn Tyr Asp Lys Gly Leu Leu Lys Thr Val Phe Ser Lys Gly Ala
130                 135                 140

Pro Tyr Gln Thr Val Thr Asp Val Glu Glu Pro Lys Thr Phe His Ile
145                 150                 155                 160

Val Gln Asn Asn Asn Ile Val Tyr Gly Cys Asn Val Tyr Met Asp Lys
                165                 170                 175

Phe Phe Glu Val Glu Asn Lys Asp Gly Ser Thr Thr Glu Ile Gly Leu
            180                 185                 190

Cys Leu Asp Phe Phe Asp Ser Tyr Lys Ile Ile Thr Cys Ala Glu Ser
        195                 200                 205

Gln Phe His Asn Tyr Val His Asp Val Asp Pro Met Phe Tyr Lys Met
    210                 215                 220

Gly Glu Glu Tyr Asp Tyr Asp Thr Trp Arg Ser Pro Thr His Lys Gln
225                 230                 235                 240

Thr Thr Leu Glu Leu Arg Tyr Gln Tyr Asn Asp Ile Tyr Met Leu Arg
                245                 250                 255

Glu Val Ile Glu Gln Phe Tyr Ile Asp Gly Leu Cys Gly Gly Glu Leu
            260                 265                 270

Pro Leu Thr Gly Met Arg Thr Ala Ser Ser Ile Ala Phe Asn Val Leu
        275                 280                 285

Lys Lys Met Thr Phe Gly Glu Glu Lys Thr Glu Glu Gly Tyr Ile Asn
    290                 295                 300

Tyr Phe Glu Leu Asp Lys Lys Thr Lys Phe Glu Phe Leu Arg Lys Arg
305                 310                 315                 320

Ile Glu Met Glu Ser Tyr Thr Gly Gly Tyr Thr His Ala Asn His Lys
                325                 330                 335

Ala Val Gly Lys Thr Ile Asn Lys Ile Gly Cys Ser Leu Asp Ile Asn
            340                 345                 350

Ser Ala Tyr Pro Ser Gln Met Ala Tyr Lys Val Phe Pro Tyr Gly Lys
        355                 360                 365

Pro Val Arg Lys Thr Trp Gly Arg Lys Pro Lys Thr Glu Lys Asn Glu
370                 375                 380

Val Tyr Leu Ile Glu Val Gly Phe Asp Phe Val Glu Pro Lys His Glu
385                 390                 395                 400

Glu Tyr Ala Leu Asp Ile Phe Lys Ile Gly Ala Val Asn Ser Lys Ala
                405                 410                 415

Leu Ser Pro Ile Thr Gly Ala Val Ser Gly Gln Glu Tyr Phe Cys Thr
            420                 425                 430

Asn Ile Lys Asp Gly Lys Ala Ile Pro Val Tyr Lys Glu Leu Lys Asp
        435                 440                 445

Thr Lys Leu Thr Thr Asn Tyr Asn Val Val Leu Thr Ser Val Glu Tyr
    450                 455                 460

Glu Phe Trp Ile Lys His Phe Asn Phe Gly Val Phe Lys Lys Asp Glu
465                 470                 475                 480

Tyr Asp Cys Phe Glu Val Asp Asn Leu Glu Phe Thr Gly Leu Lys Ile
                485                 490                 495

Gly Ser Ile Leu Tyr Tyr Lys Ala Glu Lys Gly Lys Phe Lys Pro Tyr
            500                 505                 510

Val Asp His Phe Met Lys Met Lys Val Glu Asn Lys Lys Leu Gly Asn
        515                 520                 525

Lys Pro Leu Thr Asn Gln Phe Lys Leu Ile Leu Asn Gly Ala Tyr Gly
    530                 535                 540

Lys Phe Gly Thr Lys Gln Asn Lys Glu Glu Lys Asp Leu Ile Met Asp
545                 550                 555                 560

Lys Asn Gly Leu Leu Thr Phe Thr Gly Ser Val Thr Glu Tyr Glu Gly
                565                 570                 575

Lys Glu Phe Tyr Arg Pro Tyr Ala Ser Phe Val Thr Ala Tyr Gly Arg
            580                 585                 590

Leu Gln Leu Trp Asn Ala Ile Ile Tyr Ala Val Gly Val Glu Asn Phe
        595                 600                 605

Leu Tyr Cys Asp Thr Asp Ser Ile Tyr Cys Asn Arg Glu Val Asn Ser
    610                 615                 620

Leu Ile Glu Asp Met Asn Ala Ile Gly Glu Thr Ile Asp Lys Thr Ile
625                 630                 635                 640

Leu Gly Lys Trp Asp Val Glu His Val Phe Asp Lys Phe Lys Val Leu
                645                 650                 655

Gly Gln Lys Lys Tyr Met Tyr His Asp Cys Lys Glu Asp Lys Thr Asp
            660                 665                 670

Leu Lys Cys Cys Gly Leu Pro Ser Asp Ala Arg Lys Ile Ile Ile Gly
        675                 680                 685

Gln Gly Phe Asp Glu Phe Tyr Leu Gly Lys Asn Val Glu Gly Lys Lys
    690                 695                 700

Gln Arg Lys Lys Val Ile Gly Gly Cys Leu Leu Asp Thr Leu Phe
705                 710                 715                 720

Thr Ile Lys Lys Ile Met Phe
                725

<210> SEQ ID NO 12
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 'Gly Gly Gly    Gly Ser' repeating units

<400> SEQUENCE: 12

Gly Gly Gly Gly Ser Gly Gly Gly Gly Ser Gly Gly Gly Gly Ser
1               5                  10                  15

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Lys Leu Gly
1               5

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttggtttcat tcgg                                                           14
```

EXONUCLEASE DEFICIENT POLYMERASES

RELATED APPLICATIONS

The present application claims the benefit of U.S. Provisional Patent Application Ser. No. 62/301,475, filed Feb. 29, 2016, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 20, 2017, is named 04338_529US1_SL.TXT and is 31,202 bytes in size.

TECHNICAL FIELD

Provided herein, among other things, are modified DNA polymerases that are exonuclease deficient but have the same or improved strand displacement capability as compared to the wild-type polymerase, and which are advantageous for use in industrial or research applications.

BACKGROUND

DNA polymerases are a family of enzymes that use single-stranded DNA as a template to synthesize the complementary DNA strand. In particular, DNA polymerases can add free nucleotides to the 3' end of a newly-forming strand resulting in elongation of the new strand in a 5' to 3' direction. Most DNA polymerases are multifunctional proteins that possess both polymerizing and exonucleolytic activities. For example, many DNA polymerases have 3'→5' exonuclease activity. These polymerases can recognize an incorrectly incorporated nucleotide and the 3'→5' exonuclease activity of the enzyme allows the incorrect nucleotide to be excised (this activity is known as proofreading). Following nucleotide excision, the polymerase can re-insert the correct nucleotide and replication can continue. Many DNA polymerases also have 5'→3' exonuclease activity.

Sequencing by synthesis (SBS) determines the identity of the nucleotide sequence in a DNA strand. Polymerases used in SBS not only add nucleotides to the growing strand but also proofread the growing nucleotide strand. A 3'→5' proofreading exonuclease domain is intrinsic to most DNA polymerases. As noted above, the exonuclease proofreading function can correct an incorrect base. In SBS, this exonuclease activity while sequencing will contribute towards deletion/insertion errors and is therefore undesirable. Standard mutations in the exonuclease domain to knock-out exonuclease activity in Family B polymerases typically reduce the strand displacement capability of the polymerase.

Therefore, there is a need for an exonuclease deficient polymerase that has an altered strand displacement characteristic relative to the standard mutations. Specifically, an exonuclease deficient polymerase with the same or improved strand displacement as a wild-type parental polymerase is desired. Improving strand displacement improves waiting time between consecutive nucleotide incorporations (i.e., decreases waiting time) as well as the extension/sequencing rate of the polymerase (i.e., increases the extension/sequencing rate).

BRIEF SUMMARY OF THE INVENTION

The present invention provides modified DNA polymerases (e.g., mutants) that are exonuclease deficient. The modified polymerases have the same or improved strand displacement capability as compared to the wild-type polymerase. The select mutations confer advantageous phenotypes under conditions used in industrial or research applications, e.g., catalyzing incorporation of modified polyphosphate nucleotides, e.g., tagged nucleotides, under high salt concentrations.

In an aspect there is provided a modified DNA polymerase that is exonuclease deficient, wherein the modified polymerase has an amino acid sequence of at least 80% sequence identity to the amino acid sequence as set forth in SEQ ID NO: 1. In an embodiment, the modified polymerase comprises a substitution at a position corresponding to T45, H123, L125, W127, D128, V179, S211, Y212, I215, T216, E219, Q221, E239, D241, Y242, Y259, Q260, A292, S293, S294 and combinations thereof. In some embodiments, the modified DNA polymerase retains the same or improved strand displacement capability as compared to the wild-type polymerase. In some embodiments, the modified polymerase has the same or improved strand displacement capability as compared to the parental polymerase. The parental polymerase is selected from SEQ ID NO: 1, 11, or any polymerase listed in Table 1. The parental polymerase has at least 70%, 75%, 80%, 85%, 90%, preferably 95%, 96%, 97%, 98% or 99%, or more sequence identity to SEQ ID NO: 1.

In some embodiments, the modified polymerase comprises a substitution corresponding to a substitution selected from L125K, D128H, V179Y, V179R, S211F, Y212K, I215L, T216K, Q221R, Y242G/A/L/S, Y259G/K/Q, A292K, S293G, and S294T. In an embodiment, the modified polymerase comprises a substitution corresponding to L125K. In an embodiment, the modified polymerase comprises a substitution corresponding to D128H. In an embodiment, the modified polymerase comprises a substitution corresponding to V179Y. In an embodiment, the modified polymerase comprises a substitution corresponding to V179R. In an embodiment, the modified polymerase comprises a substitution corresponding to S211F. In an embodiment, the modified polymerase comprises a substitution corresponding to Y212K. In an embodiment, the modified polymerase comprises a substitution corresponding to I215L. In an embodiment, the modified polymerase comprises a substitution corresponding to T216K. In an embodiment, the modified polymerase comprises a substitution corresponding to Q221R. In an embodiment, the modified polymerase comprises a substitution corresponding to Y242G. In an embodiment, the modified polymerase comprises a substitution corresponding to Y242A. In an embodiment, the modified polymerase comprises a substitution corresponding to Y242L. In an embodiment, the modified polymerase comprises a substitution corresponding to Y242S. In an embodiment, the modified polymerase comprises a substitution corresponding to Y259G. In an embodiment, the modified polymerase comprises a substitution corresponding to Y259K. In an embodiment, the modified polymerase comprises a substitution corresponding to Y259Q. In an embodiment, the modified polymerase comprises a substitution corresponding to A292K. In an embodiment, the modified polymerase comprises a substitution corresponding to S293G. In an embodiment, the modified polymerase comprises a substitution corresponding to S294T.

In some embodiments, the modified polymerase is selected from T529M+S366A+A547F+Y242G/A/L/S, T529M+S366A+A547F+Y259G/K/Q, T529M+S366A+

A547F+D128H, T529M+S366A+A547F+Y212G, or T529M+S36A+A547F+Y212K.

In one embodiment the invention provides a modified polymerase that has an extension rate that is greater than the parental polymerase. In some embodiments, the extension rate of the modified polymerase is between 1.5 to 5 times greater than the parental polymerase. In some embodiments, the extension rate is at least 1.5, at least 2, or at least 3 times greater than the parental polymerase.

In another embodiment, the modified polymerase has a median waiting time that is shorter when compared to the polymerase according to SEQ ID NOs: 1 or 11. In an embodiment, the modified polymerase has a median waiting time that is shorter when compared to the polymerase according to SEQ ID NO: 1. In an embodiment, the modified polymerase has a median waiting time that is shorter when compared to the polymerase according to SEQ ID NO: 11. In an embodiment, the modified polymerase has a median waiting time that is less than 3 seconds.

In all embodiments, the polymerase variant has an amino acid sequence having at least 70%, 75%, 80%, 85%, 90%, preferably 95%, 96%, 97%, 98% or 99%, or more sequence identity to SEQ ID NO: 1.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

DETAILED DESCRIPTION

Figure 1:
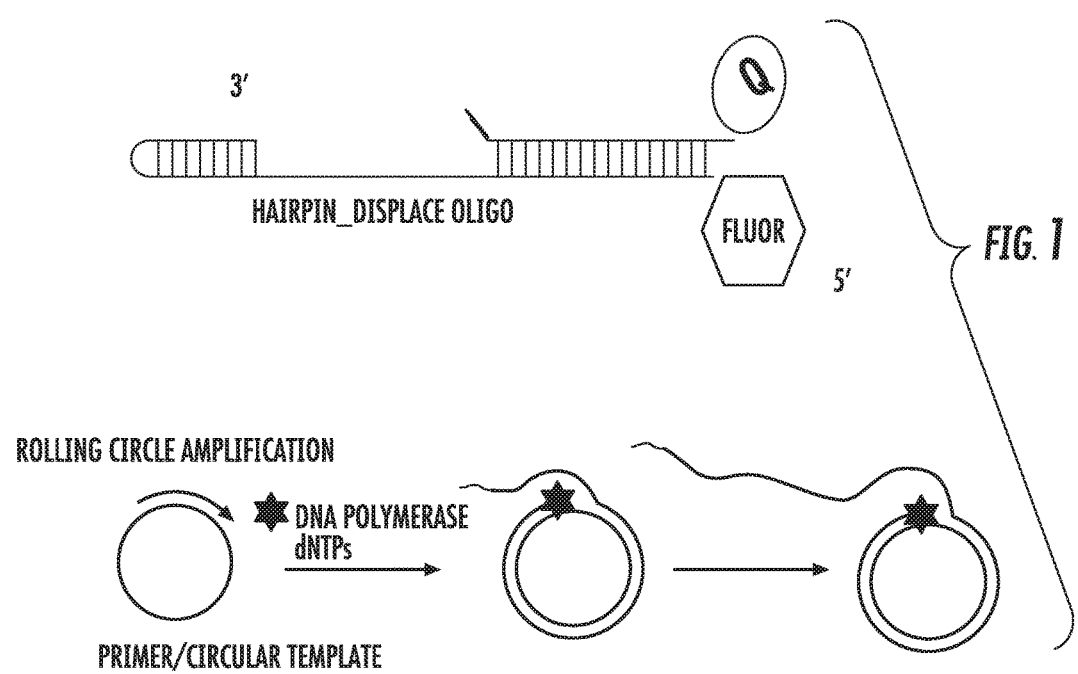
FIG. 1 illustrates an exemplary template used in either the exonuclease assay or displacement assay (upper panel). Reference is made to Examples 3 and 4. The lower panel shows a rolling circle essay. Reference is made to Example 5.

The invention will now be described in detail by way of reference only using the following definitions and examples.

All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide. It should be noted that all amino acid residue sequences are represented herein by formulae whose left and right orientation is in the conventional direction of amino-terminus to carboxy-terminus.

Base Pair (bp): As used herein, base pair refers to a partnership of adenine (A) with thymine (T), or of cytosine (C) with guanine (G) n a double stranded DNA molecule.

Complementary: As used herein, the term "complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

DNA binding affinity: As used herein, the term "DNA-binding affinity" typically refers to the activity of a DNA polymerase in binding DNA nucleic acid. In some embodiments, DNA binding activity can be measured in a two band-shift assay. See, e.g., Sambrook et al. (2001) Molecular Cloning: A Laboratory Manual ($3^{rd}$ ed., Cold Spring Harbor Laboratory Press, NY) at 9.63-9.75 (describing end-labeling of nucleic adds). A reaction mixture is prepared containing at least about 0.5 µg of the polypeptide in about 10 µl of binding buffer (50 mM sodium phosphate buffer (pH 8.0), 10% glycerol, 25 mM KCl, 25 mM $MgCl_2$). The reaction mixture is heated to 37° C. for 10 min. About $1 \times 10^4$ to $5 \times 10^4$ cpm (or about 0.5-2 ng) of the labeled double-stranded nucleic acid is added to the reaction mixture and incubated for an additional 10 min. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double-stranded nucleic acid indicates formation of a binding complex between the polypeptide and the double-stranded nucleic acid. Such nucleic acid binding activity may be quantified using standard densitometric methods to measure the amount of radioactivity in the binding complex relative to the total amount of radioactivity in the initial reaction mixture. Other methods of measuring DNA binding affinity are known in the art (see, e.g., Kong et al. (1993) J. Biol. Chem. 268(3):1965-1975).

Elongation rate: As used herein, the term "elongation rate" refers to the average rate at which a DNA polymerase extends a polymer chain. As used herein, a high elongation rate refers to an elongation rate higher than 2 nt/s (e.g., higher than 30, 35, 40, 45, 50, 55, 60, 65, 70, 75, 80, 85, 90, 95, 100, 105, 110, 115, 120, 125, 130, 135, 140 nt/s). As used in this application, the terms "elongation rate", "extension rate" and "incorporation rate" are used interchangeably.

Enzyme activity: As used herein, the term "enzyme activity" refers to the specificity and efficiency of a DNA polymerase. Enzyme activity of a DNA polymerase is also referred to as "polymerase activity," which typically refers to the activity of a DNA polymerase in catalyzing the template-directed synthesis of a polynucleotide. Enzyme activity of a polymerase can be measured using various techniques and methods known in the art. For example, serial dilutions of polymerase can be prepared in dilution buffer (e.g., 20 mM Tris.Cl, pH 8.0, 50 mM KCl, 0.5% NP 40, and 0.5% Tween-20). For each dilution, 5 µl can be removed and added to 45 µl of a reaction mixture containing 25 mM TAPS (pH 9.25), 50 mM KCl, 2 mM $MgCl_2$, 0.2 mM dATP, 0.2 mM dGTP, 0.2 mM dTTP, 0.1 mM dCTP, 12.5 µg activated DNA, 100 µM [$\alpha$-$^{32}$P]dCTP (0.05 µCi/nmol) and sterile deionized water. The reaction mixtures can be incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot can be removed from each reaction mixture. Unincorporated radioactively labeled dCTP can be removed from each aliquot by gel filtration (Centri-Sep, Princeton Separations, Adelphia, N.J.). The column eluate can be mixed with scintillation fluid (1 ml). Radioactivity in the column eluate is quantified with a scintillation counter to determine the amount of product synthesized by the polymerase. One unit of polymerase activity can be defined as the amount of polymerase necessary to synthesize 10 nmole of product in 30 minutes (Lawyer at al. (1989) J. Biol. Chem. 264:6427-647). Other methods of measuring polymerase activity are known in the art (see, e.g. Sambrook at al. (2001) Molecular Cloning: A Laboratory Manual (3rd ed., Cold Spring Harbor Laboratory Press, NY)).

Purified: As used herein, "purified" means that a molecule is present in a sample at a concentration of at least 90% by weight, or at least 95% by weight, or at least 98% by weight of the sample in which it is contained.

Isolated: An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromasomally or at a chromosomal location that is different from its natural chromosomal location.

% homology: The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, S. F., et al., Nucleic Acids Res. 25:3389-3402, 1997.)

A preferred alignment of selected sequences in order to determine "% identity" between two or more sequences, is performed using for example, the CLUSTAL-W program in MacVector version 13.0.7, operated with default parameters, including an open gap penalty of 10.0, an extended gap penalty of 0.1, and a BLOSUM 30 similarity matrix.

Modified DNA polymerase: As used herein, the term "modified DNA polymerase" refers to a DNA polymerase originated from another (i.e., parental) DNA polymerase and contains one or more amino acid alterations (e.g., amino acid substitution, deletion, or insertion) compared to the parental DNA polymerase. In some embodiments, a modified DNA polymerases of the invention is originated or modified from a naturally-occurring or wild-type DNA polymerase. In some embodiments, a modified DNA polymerase of the invention is originated or modified from a recombinant or engineered DNA polymerase including, but not limited to, chimeric DNA polymerase, fusion DNA polymerase or another modified DNA polymerase. Typically, a modified DNA polymerase has at least one changed phenotypes compared to the parental polymerase.

Mutation: As used herein, the term "mutation" refers to a change introduced into a parental sequence, including, but not limited to, substitutions, insertions, deletions (including truncations). The consequences of a mutation include, but are not limited to, the creation of a new or altered character, property, function, phenotype or trait not found in the protein encoded by the parental sequence. Some mu Mutant: As used herein, the term "mutant" refers to a modified protein which displays altered characteristics when compared to the parental protein. The terms "variant" and "mutant" are used interchangeably herein.

Wild-type: As used herein, the term "wild-type" refers to a gene or gene product which has the characteristics of that gene or gene product when isolated from a naturally-occurring source.

Fidelity: As used herein, the term "fidelity" refers to either the accuracy of DNA polymerization by template-dependent DNA polymerase or the measured difference in $k_{off}$ of the correct nucleotide vs incorrect nucleotide binding to the template DNA. The fidelity of a DNA polymerase is typically measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate less than $4.45 \times 10^{-6}$ (e.g., less than $4.0 \times 10^{-6}$, $3.5 \times 10^{-6}$, $3.0 \times 10^{-6}$, $2.5 \times 10^{-6}$, $2.0 \times 10^{-6}$, $1.5 \times 10^{-6}$, $1.0 \times 10^{-6}$, $0.5 \times 10^{-6}$) mutations/nt/doubling. The fidelity or error rate of a DNA polymerase may be measured using assays known to the art. For example, the error rates of DNA polymerases can be tested as described herein or as described in Johnson, et al., Biochim Biophys Acta. 2010 May; 1804(5): 1041-1048.

Nanopore: The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha-hemolysin, MspA are examples of a protein nanopore.

Nucleotide: As used herein, a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence," and is represented herein by a formula whose left to right orientation is in the conventional direction of 5'-terminus to 3'-terminus. As used herein, a "modified nucleotide" refers to a polyphosphate, e.g., 3, 4, 5, 6, 7 or 8 phosphates, nucleotide.

Oligonucleotide or Polynucleotide: As used herein, the term "oligonucleotide" is defined as a molecule including two or more deoxyribonucleotides and/or ribonucleotides, preferably more than three. Its exact size will depend on many factors, which in turn depend on the ultimate function or use of the oligonucleotide. The oligonucleotide may be derived synthetically or by cloning. As used herein, the term "polynucleotide" refers to a polymer molecule composed of nucleotide monomers covalently bonded in a chain. DNA (deoxyribonucleic acid) and RNA (ribonucleic acid) are examples of polynucleotides.

Polymerase: As used herein, a "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. A "DNA polymerase" catalyzes the polymerization of deoxynucleotides.

Primer: As used herein, the term "primer" refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and thermostable enzyme in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the thermostable enzyme. The exact lengths of the primers will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

Processivity: As used herein, "processivity" refers to the ability of a polymerase to remain attached to the template and perform multiple modification reactions. "Modification reactions" include but are not limited to polymerization, and exonucleolytic cleavage. In some embodiments, "proressivity" refers to the ability of a DNA polymerase to perform a sequence of polymerization steps without intervening dissociation of the enzyme from the growing DNA chains. Typically, "processivity" of a DNA polymerase is measured by the length of nucleotides (for example 20 nts, 300 nts, 0.5-1 kb, or more) that are polymerized or modified without intervening dissociation of the DNA polymerase from the growing DNA chain. "Processivity" can depend on the nature of the polymerase, the sequence of a DNA template, and reaction conditions, for example, salt concentration, temperature or the presence of specific proteins. As used herein, the term "high processivity" refers to a processivity higher than 20 nts (e.g., higher than 40 nts, 60 nts, 80 nts, 100 nts, 120 nts, 140 nts, 160 nts, 180 nts, 200 nts, 220 nts, 240 nts, 260 nts, 280 nts, 300 nts, 320 nts, 340 nts, 360 its, 380 nts, 400 nts, or higher) per association/disassociation with the template. Processivity can be measured according the methods defined herein and in WO 01/92501 A1 (MJ Bioworks, Inc., Improved Nucleic Acid Modifying Enzymes, published 6 Dec. 2001).

Strand Displacement: As used herein, the term "strand displacement" means the ability of the polymerase to displace downstream DNA encountered during synthesis of a nascent DNA strand as measured using a strand displacement activity assay as described herein. DNA polymerases may have varying degrees of strand displacement activity.

Synthesis: As used herein, the term "synthesis" refers to any in vitro method for making new strand of polynucleotide or elongating existing polynucleotide (i.e., DNA or RNA) in a template dependent manner Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, PCR, the labeling of polynucleotide (i.e., for probes and oligonucleotide primers), polynucleotide sequencing.

Template DNA molecule: As used herein, the term "template DNA molecule" refers to a strand of a nucleic acid from which a complementary nucleic acid strand is synthesized by a DNA polymerase, for example, in a primer extension reaction.

Template-dependent manner: As used herein, the term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: Molecular Biology of the Gene, 4th Ed., W. A. Benjamin, Inc., Menlo Park, Calif. (1987)).

Tag: As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which signature may be detected with the aid of a nanopore.

Tagged Nucleotide: As used herein, the term "tagged nucleotide" refers to a nucleotide or modified nucleotide that has a tag attached. The tag may be attached covalently to the sugar, the phosphate (or polyphosphate) or base. The tag may be on the terminal phosphate.

Vector: As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

The polymerase variants provided for herein are useful in the chip-based polynucleotide sequencing as described in WO2013/188841 (Genia Technologies, Inc., Chip Set-Up and High-Accuracy Nucleic Acid Sequencing, published 19 Dec. 2013).

Desired characteristics of a polymerase that finds use in sequencing DNA are:
 a. Slow $k_{off}$ (for nucleotide)
 b. Fast $k_{on}$ (for nucleotide)
 c. High fidelity
 d. Low exonuclease activity
 e. DNA strand displacement
 f. $k_{chem}$
 g. Increased stability
 h. Processivity
 i. Salt tolerance
 j. Compatible with attachment to nanopore
 k. Ability to incorporate a polyphosphates having 4, 5, 6, 7 or 8 phosphates, e.g., quadraphosphate, pentaphosphate, hexaphosphate, heptaphosphate or octophosphate nucleotide
 l. Sequencing accuracy
 m. Long read lengths, i.e., long continuous reads.

Nomenclature

In the present description and claims, the conventional one-letter and three-letter codes for amino acid residues are used.

For ease of reference, polymerase variants of the application are described by use of the following nomenclature:

Original amino acid(s): position(s): substituted amino acid(s). According to this nomenclature, for instance the substitution of serine by an alanine in position 242 is shown as:

Ser242Ala or S242A

Multiple mutations are separated by plus signs, i.e.:

Ala30Asp+Glu34Ser or A30N+E34S representing mutations in positions 30 and 34 substituting alanine and glutamic acid for asparagine and serine, respectively.

When one or more alternative amino acid residues may be inserted in a given position it is indicated as: A30N/E or A30N or A30E.

Numbering of the residues, unless otherwise noted, is with reference to SEQ ID NO:2 (Pol6 with His-tag).

Site-Directed Mutagenesis of Polymerase

*Clostridium* phage phiCPV4 wild type sequences are provided herein (SEQ ID NO:3, nucleic acid coding region plus a His-tag; SEQ ID NO:1, amino acid sequence) and available elsewhere (National Center for Bioinformatics or GenBank Accession Numbers AFH27113). The parental polymerase may be selected from SEQ ID NOs: 1 or 11, or any of the following pol6 variants:

TABLE 1

| Polymerase Number | Mutations (in pol6; SEQ ID NO: 1) |
|---|---|
| 1 | N535L + N545K + T651Y |
| 2 | S366A + N535L + I652Q |
| 3 | S366A + T529M + N535L |
| 4 | S366A + N535L + N545K |
| 5 | S366A + N535L + A547M |
| 6 | S366A + P542E + I652Q |
| 7 | S366A + P542E + N545K |

TABLE 1-continued

| Polymerase Number | Mutations (in pol6; SEQ ID NO: 1) |
|---|---|
| 8 | S366A + P542E + T651Y |
| 9 | P542E + N545K + T651Y |
| 10 | P542E + Q546W + T651Y |
| 11 | N535L + T651Y |
| 12 | S366A + N535L |
| 13 | N535L + N545K + T651Y + T529M |
| 14 | N535L + N545K + T651Y + N635D |
| 15 | N535L + N545K + T651Y + I652Q |
| 16 | S366A + N535L + I652Q + T529M |
| 17 | N535L + N545K + T651Y + T647G |
| 18 | S366A + N535L + I652Q + A547Y |
| 19 | S366A + N535L + A547M + T647G |
| 20 | S366A + N535I + I652Q |
| 21 | N535I + N545K + T651Y + T529M |
| 22 | N535I + N545K + T651Y + N635D |
| 23 | N535I + N545K + T851Y + I652Q |
| 24 | N535L + N545K + T651Y + T647G + C623G |
| 25 | N535L + N545K + T651Y + T647G + I628Y |
| 26 | S366A + N535L + A547M + T647G + S360G |
| 27 | N535I + N545K + T651Y + I652Q + Y225I |
| 28 | N535L + N545K + T651Y + T647G + K655G |
| 29 | N535L + N545K + T651Y + T647G + L549Q |
| 30 | S366A + N535L + I652Q + A547Y + K655G |
| 31 | T647G + A547F + Y225T |
| 32 | A547F + A610T + S366A |
| 33 | A547F + A610T + Y225I |
| 34 | S366A + T647G + A547F |
| 35 | T651Y + S366A + A547F |
| 36 | T529M + S366A + A547F (SEQ ID NO: 8) |
| 37 | T647E + S366A + A547F |
| 38 | T529M + T647G + A547F |
| 39 | N545K + S366A + A547F |
| 40 | T647G + A547F + T529M |
| 41 | N545K + T647G + A547F |
| 42 | T529M + A610T + A547F |
| 43 | M641Y + T529M + A547F |
| 44 | T647G + C623G + A547F |
| 45 | A610T + I295W + T651Y |
| 46 | V615A + M531Y + T647G |
| 47 | T529M + S366A + A547F + N545K |
| 48 | T529M + S366A + A547F + N545R |
| 49 | T529M + S366A + A547F + N552L |
| 50 | T529M + S366A + A547F + Y629W |
| 51 | T529M + S366A + A547F + N545L + Y629W |
| 52 | T529M + S366A + A547F + N545L + Y225L |
| 53 | T529M + S366A + A547F + N545L + Y225F |
| 54 | T529M + S366A + A547F + N545L + K655F |
| 55 | T529M + S366A + A547F + N545L + N552L |
| 56 | T529M + S366A + A547F + N545R + M531A |
| 57 | T529M + S366A + A547F + N545R + G539Y |
| 58 | T529M + S366A + A547F + N545R + V658L |
| 59 | T529M + S366A + A547F + N545L + Y225L + D657R |
| 60 | T529M + S366A + A547F + N545L + Y225L + N552L |
| 61 | T529M + S366A + A547F + N545L + Y225L + I652G |
| 62 | T529M + S366A + A547F + N545L + Y225L + I652Q |
| 63 | T529M + S366A + A547F + N545L + Y225L + N552M |
| 64 | T529M − S366A − A547F − N545L − Y225L − N552L − Y524F |
| 65 | T529M − S366A − A547F − N545L − Y225L − N552L − S369Y |

Point mutations may be introduced using QuikChange Lightning 2 kit (Stategene/Agilent) following manufacturer's instructions or NEB Q5 mutagenesis protocol.

In an embodiment, the variant polymerase having altered enzyme activity, as compared to SEQ ID NOs:1, 8 or a parental polymerase, has a mutation selected from a. T45G/A/L/E/Q/K/H/S/Y/R/W/T/M/F, b. H123G/A/L/E/Q/K/H/S/Y/R/W/T/M/F, c. L125G/A/L/E/Q/K/H/S/Y/R/W/T/M/F, d. W127G/A/L/E/Q/K/H/S/Y/R/W/T/M/F, e. D128G/A/L/E/Q/K/H/S/Y/R/W/T/M/F, f. Y212G/A/L/E/Q/K/H/S/Y/R/W/T/M/F, g. E219G/A/L/E/Q/K/H/S/Y/R/W/T/M/F, h. E239G/A/L/E/Q/K/H/S/Y/R/W/T/M/F, i. D241G/A/L/E/Q/K/H/S/Y/R/W/T/M/F, j. Y242G/A/L/E/Q/K/H/S/Y/R/W/T/M/F, k. Y259G/A/L/E/Q/K/H/S/Y/R/W/T/M/F, or l. Q260G/A/L/E/Q/K/H/S/Y/R/W/T/M/F.

Primers can be ordered from commercial companies, e.g., IDT DNA.

Nanopore Assembly and Insertion

The methods described herein can use a nanopore having a polymerase attached to the nanopore. In some cases, it is desirable to have one and only one polymerase per nanopore (e.g., so that only one nucleic acid molecule is sequenced at each nanopore). However, many nanopores, including, e.g., alpha-hemolysin (aHL), can be multimeric proteins having a plurality of subunits (e.g., 7 subunits for aHL). The subunits can be identical copies of the same polypeptide. Provided herein are multimeric proteins (e.g., nanopores) having a defined ratio of modified subunits (e.g., a-HL variants) to un-modified subunits (e.g., a-HL). Also provided herein are methods for producing multimeric proteins (e.g., nanopores) having a defined ratio of modified subunits to un-modified subunits.

With reference to FIG. 27 of WO2014/074727 (Genie Technologies, Inc.), a method for assembling a protein having a plurality of subunits comprises providing a plurality of first subunits 2705 and providing a plurality of second subunits 2710, where the second subunits are modified when compared with the first subunits. In some cases, the first subunits are wild-type (e.g., purified from native sources or produced recombinantly). The second subunits can be modified in any suitable way. In some cases, the second subunits have a protein (e.g., a polymerase) attached (e.g., as a fusion protein).

The modified subunits can comprise a chemically reactive moiety (e.g., an azide or an alkyne group suitable for forming a linkage). In some cases, the method further comprises performing a reaction (e.g., a Click chemistry cycloaddition) to attach an entity (e.g., a polymerase) to the chemically reactive moiety.

The method can further comprise contacting the first subunits with the second subunits 2715 in a first ratio to form a plurality of proteins 2720 having the first subunits and the second subunits. For example, one part modified aHL subunits having a reactive group suitable for attaching a polymerase can be mixed with six parts wild-type aHL subunits (i.e., with the first ratio being 1:6). The plurality of proteins can have a plurality of ratios of the first subunits to the second subunits. For example, the mixed subunits can form several nanopores having a distribution of stoichiometries of modified to un-modified subunits (e.g., 1:6, 2:5, 3:4).

In some cases, the proteins are formed by simply mixing the subunits. In the case of aHL nanopores for example, a detergent (e.g., ceoxycholic acid) can trigger the aHL monomer to adopt the pore conformation. The nanopores can also be formed using a lipid (e.g., 1,2-duphytanoyl-sn-glycero- 3-phosphocholine (DPhPC) or 1,2-di-O-phytanyl-sn-glycero-3-phosphocholine (DoPhPC)) and moderate temperature (e.g., less than about 100° C.). In some cases, mixing DPhPC with a buffer solution creates large multi-lamellar vesicles (LMV), and adding aHL subunits to this solution and incubating the mixture at 40° C. for 30 minutes results in pore formation.

If two different types of subunits are used (e.g., the natural wild type protein and a second aHL monomer which can contain a single point mutation), the resulting proteins can have a mixed stoichiometry (e.g., of the wild type and mutant proteins). The stoichiometry of these proteins can follow a formula which is dependent upon the ratio of the concentrations of the two proteins used in the pore forming reaction. This formula is as follows:

$$100P_m = 100[n!/m!(n-m)!] \cdot f_{mut}^m \cdot f_{wt}^{n-m}, \text{ where}$$

$P_m$=probability of a pore having m number of mutant subunits n=total number of subunits (e.g., 7 for aHL)

m=number of "mutant" subunits $f_{mut}$=fraction or ratio of mutant subunits mixed together $f_{wt}$=fraction or ratio of wild-type subunits mixed together The method can further comprise fractionating the plurality of proteins to enrich proteins that have a second ratio of the first subunits to the second subunits 2725. For example, nanopore proteins can be isolated that have one and only one modified subunit (e.g., a second ratio of 1:6). However, any second ratio is suitable. A distribution of second ratios can also be fractionated such as enriching proteins that have either one or two modified subunits. The total number of subunits forming the protein is not always 7 (e.g., a different nanopore can be used or an alpha-hemolysin nanopore can form having six subunits) as depicted in FIG. 27 of WO2014/074727. In some cases, proteins having only one modified subunit are enriched. In such cases, the second ratio is 1 second subunit per (n−1) first subunits where n is the number of subunits comprising the protein.

The first ratio can be the same as the second ratio, however this is not required. In some cases, proteins having mutated monomers can form less efficiently than those not having mutated subunits. If this is the case, the first ratio can be greater than the second ratio (e.g., if a second ratio of 1 mutated to 6 non-mutated subunits are desired in a nanopore, forming a suitable number of 1:6 proteins may require mixing the subunits at a ratio greater than 1:6).

Proteins having different second ratios of subunits can behave differently (e.g., have different retention times) in a separation. In some cases, the proteins are fractionated using chromatography, such as ion exchange chromatography or affinity chromatography. Since the first and second subunits can be identical apart from the modification, the number of modifications on the protein can serve as a basis for separation. In some cases, either the first or second subunits have a purification tag (e.g., in addition to the modification) to allow or improve the efficiency of the fractionation. In some cases, a poly-histidine tag (His-tag), a streptavidin tag (Strep-tag), or other peptide tag is used. In some instances, the first and second subunits each comprise different tags and the fractionation step fractionates on the basis of each tag. In the case of a His-tag, a charge is created on the tag at low pH (Histidine residues become positively charged below the pKa of the side chain). With a significant difference in charge on one of the aHL molecules compared to the others, ion exchange chromatography can be used to separate the oligomers which have 0, 1, 2, 3, 4, 5, 6, or 7 of the "charge-tagged" aHL subunits. In principle, this charge tag can be a string of any amino acids which carry a uniform charge. FIG. 28 and FIG. 29 show examples of fractionation of nanopores based on a His-tag. FIG. 28 shows a plot of ultraviolet absorbance at 280 nanometers, ultraviolet absorbance at 260 nanometers, and conductivity. The peaks correspond to nanopores with various ratios of modified and unmodified subunits. FIG. 29 of WO2014/074727 shows fractionation of aHL nanopores and mutants thereof using both His-tag and Strop-tags.

In some cases, an entity (e.g., a polymerase) is attached to the protein following fractionation. The protein can be a nanopore and the entity can be a polymerase. In some instances, the method further comprises inserting the proteins having the second ratio subunits into a bilayer.

In some situations, a nanopore can comprise a plurality of subunits. A polymerase can be attached to one of the subunits and at least one and less than all of the subunits comprise a first purification tag. In some examples, the nanopore is alpha-hemolysin or a variant thereof. In some instances, all of the subunits comprise a first purification tag or a second purification tag. The first purification tag can be a poly-histidine tag (e.g., on the subunit having the polymerase attached).

Polymerase Attached to Nanopore

In some cases, a polymerase (e.g., DNA polymerase) is attached to and/or is located in proximity to the nanopore. The polymerase can be attached to the nanopore before or after the nanopore is incorporated into the membrane. In some instances, the nanopore and polymerase are a fusion protein (i.e., single polypeptide chain).

The polymerase can be attached to the nanopore in any suitable way. In some cases, the polymerase is attached to the nanopore (e.g., hemolysin) protein monomer and then the full nanopore heptamer is assembled (e.g., in a ratio of one monomer with an attached polymerase to 6 nanopore (e.g., hemolysin) monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Other linkers that may find use in attaching the polymerase to a nanopore are direct genetic linkage (e.g., (GGGGS)$_{1-3}$ amino acid linker (SEQ ID NO: 12)), transglutaminase mediated linking (e.g., RSKLG (SEQ ID NO: 13)), sortase mediated linking, and chemical linking through cysteine modifications. Specific linkers contemplated as useful herein are (GGGGS)$_{1-3}$ (SEQ ID NO: 12), K-tag (RSKLG (SEQ ID NO: 13)) on N-terminus, ΔTEV site (12-25), ΔTEV site+N-terminus of SpyCatcher (12-49).

Apparatus Set-Up

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). See, for example, WO 2013123450, for the apparatus and device set-up for sensing a nucleotide or tag.

Pore based sensors (e.g., biochips) can be used for electro-interrogation of single molecules. A pore based sensor can include a nanopore of the present disclosure formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μL or μl (microliters); cm (centimeters); mm (millimeters); μm (micrometers); nm (nanometers); ° C. (degrees Centigrade); h (hours); min (minutes); sec (seconds); msec (milliseconds); dN6P (deoxy nucleotide hexaphosphates).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

The parental polymerase for examples 3-5 was SEQ ID NO: 1 comprising the mutations T529M+S366A+A547F (SEQ ID NO:8).

Example 1

Directed Mutagenesis

This example illustrates the introduction of a mutation into a pol6 polymerase at a desired position.

DNA encoding the His-tagged wild-type pol6 was purchased from a commercial source (DNA 2.0, Menlo Park, Calif.). The sequence was verified by sequencing.

For the mutant screen, we expressed the polymerase as is (N-ter His-Pol6). In order to test the pol hits on the chip, we engineered in a SpyCatcher domain in N-ter or C-ter of Pol6.

Rational positions to impact Pol6-exonuclease activity were identified based on homology modeling of known crystal structures.

For the primary screen, each of the rational positions were mutated into Gly, Ala, Leu, Glu, Gin. Lys, His, Tyr, Pro, Trp, Thr, Ser, Arg, Phe or Met using the Q5 mutagenesis protocol.

The primers for each mutagenesis reaction was designed using the NEB base changer protocol and ordered in 96-well plate format from IDT.

The forward and reverse primers were 5' phosphorylated in high throughput (HTP) format using the T4 polynucleotidekinase (PNK) purchased from NEB. A typical 25-μl reaction contained 15 μl of primer at 10 μM, 5 μl of 5× reaction buffer (from NEB), 1.25 μl PNK enzyme, 3.75 μl water. The reaction was performed at 37° C. for 30 min and the enzyme heat inactivated at 65° C. for 20 min.

PCR mutagenesis was performed using Q5 DNA polymerase from NEB. A typical 25 μl reaction contained 5 μl of Q5 buffer, 5 μl of GC enhancer, 0.5 ul of 10 mM dNTPs, 1.25 μl of 10 μM phosphorylated mutagenesis primers forward and reverse, 0.25 μl Q5 polymerase and 1 μl of 5 ng/ml wild type Pol6 template, i.e., His-Pol6, and 10.75 μl H$_2$O.

Once PCR is complete, 0.5 μl of Dpn1 was added to 25 μl PCR mix and incubated at 37° C. for 1 hr.

Add 2.5 μl of Dpn1 treated PCR product with 2.5 μl of Blunt/TA ligase master mix. Incubate at room temperature for 1 hr.

Add 1 μl of ligation mix to 20 ul of 96-well BL21DE3 cells (EMD Millipore) and incubate on ice for 5 min.

Heat shock at 42° C. for exactly 30 sec using the PCR device and place on ice for 2 min.

Add 80 μl of SOC and incubate at 37° C. incubator for 1 hr without shaking.

Add 100 μl of SOC or ultra pure water and plate them in 48-well LB-agar plates with 50-100 μg/ml kanamycin.

Example 2

Expression and Purification

The following example details how the pol6 variants were expressed and purified using a high throughput method.

DNA encoding the variants in the pD441 vector (expression plasmid) was transformed into competent *E. coli* and glycerol stocks made. Starting from a tiny pick of the glycerol stock, grow 1 ml starter culture in LB with 0.2% Glucose and 100 μg/ml Kanamycin for approximately 8 hrs. Transfer 25 μl of log phase starter culture into 1 ml of expression media (Terrific Broth (TB) autoinduction media supplemented with 0.2% glucose, 50 mM Potassium Phosphate, 5 mM MgCl2 and 100 μg/ml Kanamycin) in 96-deep well plates. The plates were incubated with shaking at 250-300 rpm for 36-40 hrs at 28° C.

Cells were then harvested via centrifugation at 3200×g for 30 minutes at 4° C. The media was decanted off and the cell pellet resuspended in 200 µl pre-chilled lysis buffer (20 mM Potassium Phosphate pH 7.5, 100 mM NaCl, 0.5% Tween20, 5 mM TCEP, 10 mM Imidazole, 1 mM PMSF, 1× Bug Buster, 100 µg/ml Lysozyme and protease inhibitors) and incubate at room temperature for 20 min with mild agitation. Then add 20 µl from a 10× stock to a final concentration of 100 µg/ml DNase, 5 mM MgCl2, 100 µg/ml RNase I and incubate in on ice for 5-10 min to produce a lysate. Supplement the lysate with 200 µl of 1M Potassium Phosphate, pH 7.5 (Final concentration will be about 0.5M Potassium phosphate in 400 µl lysate) and filter through Pall filter plates (Part#5053, 3 micron filters) via centrifugation at approximately 1500 rpm at 4 C for 10 minutes. The clarified lysates were then applied to equilibrated 96-well His-Pur Cobalt plates (Pierce Part#90095) and bind for 15-30 min.

The flow through (FT) was collected by centrifugation at 500×G for 3 min. The FT was then washed 3 times with 400 ul of wash buffer 1 (0.5M Potassium Phosphate pH 7.5, 1M NaCl 5 mM TCEP, 20 mM Imidazole+0.5% Tween20). The FT was then washed twice in 400 ul wash buffer 2 (50 mM Tris pH 7.4, 200 mM KCl, 5 mM TCEP, 0.5% Tween20, 20 mM Imidazole).

The Pol6 was eluted using 200 µl elution buffer (50 mM Tris Ph7.4, 200 mM KCl, 5 mM TCEP, 0.5% Tween20, 300 mM Imidazole, 25% Glycerol) and collected after 1-2 min incubation. Reapply eluate to the same His-Pur plate 2-3 times to get concentrated Pol6 in elute. The purified polymerase is >95% pure as evaluated by SDS-PAGE. The protein concentration is ~3 uM (0.35 mg/ml) with a 260/280 ratio of 0.6 as evaluated by Nanodrop.

Polymerase activity is checked by Fluorescence displacement assay (see Example 4).

Example 3

Exo Activity Assay

This example shows a method to determine the exonuclease activity of variants.

The assay is a fluorescence based assay. In the absence of nucleotides and in the presence of $Mg^{+2}$, the exonuclease activity of the polymerase is initiated. The polymerase starts removing residues one at a time from the DNA template; and as it continues to chew releases the Fluorophore from the quencher causing the signal to increase. See FIG. 1.

The sequences used were as follows:

```
Hairpin Displacement Oligo (i.e., ATTO-488
displacement template)
                                     (SEQ ID NO: 6)
5'-/5ATTO488N/AGA GTG ATA GTA TGA TTA TGT AGA TGT

AGC ATT TGA TAT GTG AGT AGC CGA ATG AAA CCT TTG

GTT TCA TTC GG 3'

Short of Complementary Oligo
                                     (SEQ ID NO: 7)
5'- TTT TCA TAT CAA ATC CTA CAT CTA CAT AAT CAT ACT ATC ACT CT/3IABkFQ/-3'
```

The fluorophore used was Atto-488. The quencher used was 3' Iowa Black® FQ. The primer is annealed to template at 1:1 ratio using the following PCR protocol:

i. 95° C. for 5 mins
ii. 93° C. for 50 sec; decrease by 2 degrees/cycle until the temperature reaches 61° C.
iii. 59° C. for 25 sec; decrease by 2 degrees/cycle until the temperature reaches 35° C. then stored at 4° C. until used.

A final 40 µl reaction mixture was prepared by mixing 20 µL Buffer A (75 mM potassium glutamate, 25 mM HEPES pH 7.5, 0.2 mM EDTA, 0.05% Triton X-100, 5 mM TCEP, 25 µg/ml BSA and 50 nM ATTO-488 displacement template (pre-annealed to the primer) (final concentration), 5 µL polymerase (Final concentration 100 nM), and 15 µL Buffer B (25 mM HEPES pH 7.5, 75 mM potassium glutamate, 0.05% Triton X-100, 5 mM TCEP, 25 µg/ml BSA, and 5 mM MgCl₂; final concentration).

Twenty (20) µL Buffer A was mixed with 5 µL polymerase and incubated for 30 minutes at room temperature. A BMG LABTECH plate reader was used and programmed such that it initiated the reaction by adding 15 µL of Buffer B and measured the increase in fluorescence every 8 seconds (excitation wavelength of 485 nm and emission wavelength of 520 nm) for a period of over 2 hours. The mutants were selected for further study if there was a decreased fluorescence signal observed over a period of 2 hours when compared to the controls.

Figure 2:
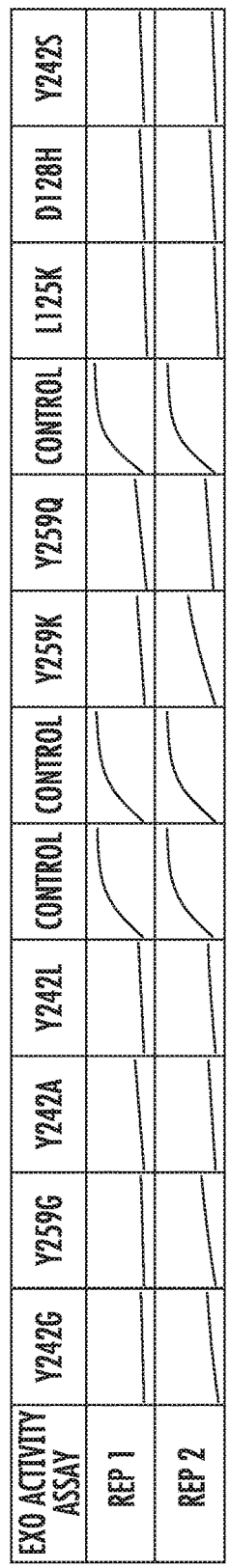
FIG. 2 shows the results of an exonuclease assay. The time course for two replicates of the indicated variants is shown. Parental polymerase served as controls. All mutated polymerases show reduced or no exonuclease activity. Reference is made to Example 3.

Results for select variants are shown in FIG. 2.

Example 4

Displacement Assay

This example shows the strand displacement activity of exonuclease deficient (exo⁻) variants.

The strand displacement polymerase assay measures the enzyme's ability to move through double stranded DNA during synthesis. This assay is based upon fluorescence, where DNA templates that haven't been extended have low fluorescence and templates that have been extended displace a piece of DNA which then allows them to emit more fluorescence than the unextended DNA template. See FIG. 1. In the presence of $Mg^{2+}$ and nucleotides, the polymerase extends along the hairpin template and displaces the quencher oligo, resulting in an increase of fluorescence.

The flourophore used was Cy5 and the quencher was 3BHQ-2. The sequences used were as follows:

```
Haipin Displacement Oligo (i.e., Cy5-Displacement
template)
                               (SEQ ID NOS 4 and 14)
5- /5Cy5/AGA GTG ATA GTA TGA TTA TGT AGA TGT AGG ATT TGA TAT GTG AGT AGC CGA ATG AAA CCT T/iSpC3/TT

GGT TTC ATT CGG-3

Short of Complementary Oligo
                                     (SEQ ID NO: 5)
5'- TTT TCA TAA TCA TAC TAT CAC TCT /3BHQ_2/-3'
```

A final 45 µL reaction mixture was prepared by mixing 23 µL Buffer A (75 mM potassium glutamate, 25 mM HEPES pH 7.5, 0.2 mM EDTA, 0.05% Triton X-100, 5 mM TCEP, 25 µg/ml BSA, Cy5 short template and 20 µM dN6P (final concentration), 4 µL polymerase (final concentration of 100 nM), 10 µL Buffer B (25 mM HEPES pH 7.5, 300 mM potassium glutamate, 0.05% Triton X-100, 55 nM TCEP, 25 µg/ml BSA, and 5 mM MgCl₂; final concentration) and 8 µL 1M potassium glutamate.

Twenty-three (23) μL of Buffer A was mixed with 4 μL of Pol and incubated it for 30 minutes at room temperature. A BMG LABTECH plate reader was used and programmed such that it adds 8 μL of 1 M K-Glu, shakes for 5 sec, waits for 5 sec and initiates the reaction by the addition of 10 μL of Buffer B and measures fluorescence (Excites at 648 nm and emits at 688 nm) every 0.1 s for 100 s.

Calculation of the time to infliction and hence the kcat were then performed.

Figure 3:
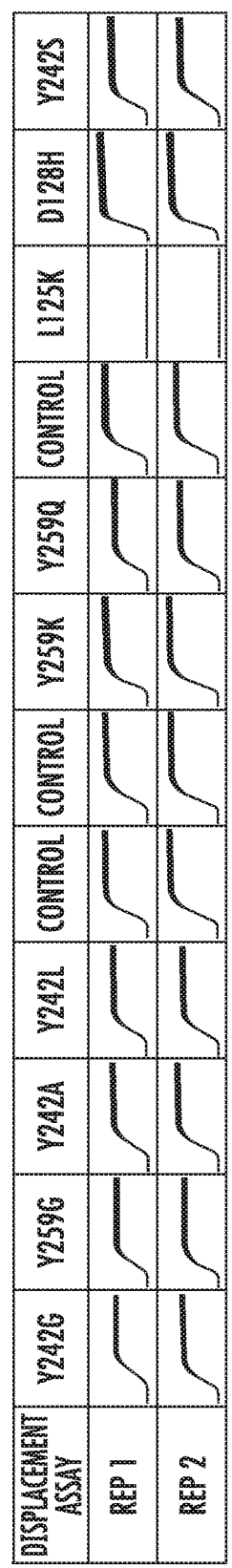
FIG. 3 shows the results of a displacement assay. The time course for two replicates of the indicated variants is shown. Controls are the same as in FIG. 1. All mutants tested except L125K show extension/displacement activity in this figure. Reference is made to Example 4.

Exemplary displacement results are shown in FIG. 3.

Example 5

Rolling Circle Assay

This example shows another method of determining strand displacement as well as the ability of the polymerase to synthesize a new strand based upon the template DNA.

The Rolling Circle Assay (RCA) is one in which a circular template DNA is used and the DNA polymerase is tested for its ability to go around the circle many times. This assay is another type of strand displacement assay and is specifically testing for the strand displacement activity of the enzyme. It is monitored by using gels to measure their migration pattern. Typically the more times the enzyme rolls around the circle the larger the piece of DNA it synthesizes and the slower the resulting fragment migrates on the gel.

A final 50 μL reaction mixture was prepaid by mixing 20 μL Buffer A (75 mM potassium glutamate, 25 mM HEPES pH 7.5, 0.2 mM EDTA, 0.05% Triton X-100, 5 mM TCEP, 25 μg/ml BSA, 100 nM HFCirc10 (in house circular template; SEQ ID NO:9) complexed with primer (SEQ ID NO:10), and 40 μM dN6P; final concentration), 10 μL polymerase, and 20 μL Buffer B (25 mM HEPES pH 7.5, 300 mM potassium glutamate, 0.05% Triton X-100, 5 mM TCEP, 25 μg/ml BSA, and 5 mM MgCl$_2$; final concentration).

Twenty (20) μL Buffer A was mixed with 10 μL of polymerase and incubated for 30 minutes at room temperature. The reaction was initiated by the addition of 20 μL Buffer B. Fifteen (15) μL of the above mix was removed at time T=0, T=20 mins and T=40 mins and added to 15 μL of Reaction Terminator (Formamide, 50 mM EDTA, Orange-G dye) to terminate the reaction. The time point samples were boiled at 95° C. for 5 minutes. Three (3) μL SYBRGold was added to the 30 μL of terminated mix. The samples were then run on a 1.2% Agarose gel at 130 V for about 65-75 mins. The gel was analyzed, and mutants that have larger and sharper product than the controls were selected for further study.

Figure 4:
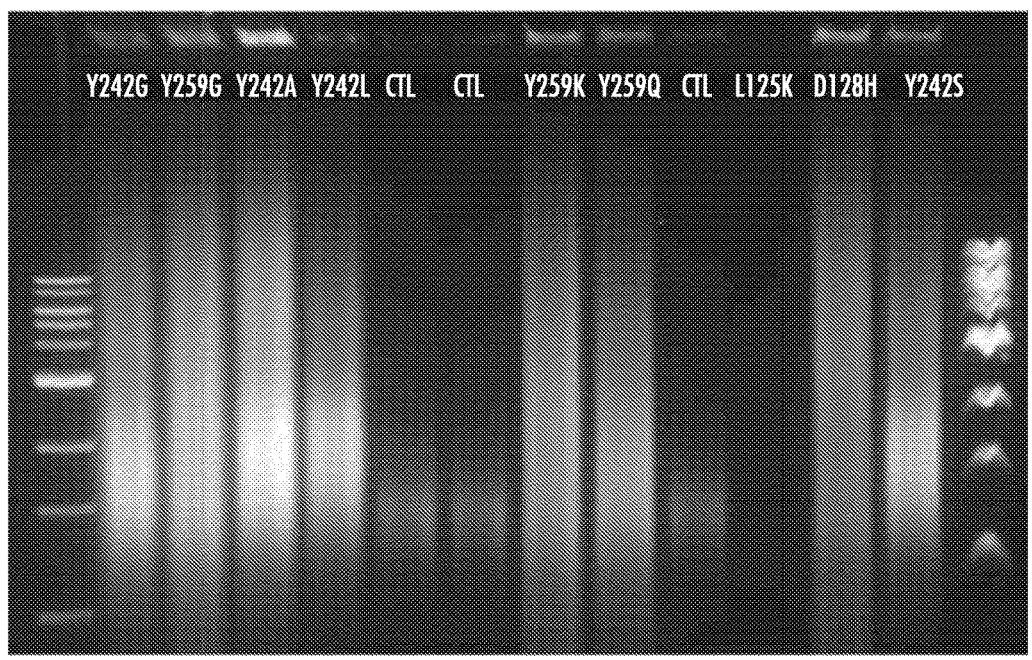
FIG. 4 shows the results of rolling circle assay. Shown is a photograph of an agarose gel. The variants except L125K show activity. The right and left lanes have the molecular ladder for reference. The yellow line represents where an expected extension product produced by the SEQ ID NO:8 polymerase would be seen. Reference is made to Example 5.
Figure 5:
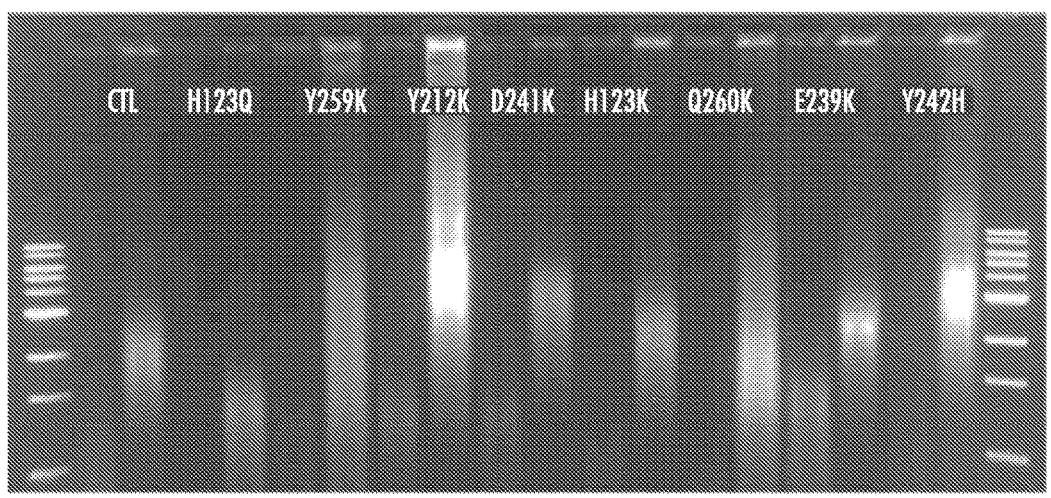
FIG. 5 shows the results of rolling circle assay. Shown is a photograph of an agarose gel. Lanes 1 and 20 have the molecular ladder or reference. Lanes 8 (F6) is Y212K. The variants are identified using the alphanumeric reference numbers shown in FIGS. 1 and 2. The yellow line represents where an expected expression product produced by the SEQ ID NO:8 polymerase would be seen. Reference is made to Example 5.

Exemplary results are shown in FIG. 4 and FIG. 5.

Example 6

On Chip Activity

This example shows that the variant polymerases have improved strand displacement properties.

The parental polymerase (SEQ ID NO: 8 or SEQ ID NO: 11) and variant polymerase (Y212K in a background of SEQ ID NO: 8 or SEQ ID NO: 11) polymerases were assayed on a biochip to determine the effect of a mutation at one or more positions of the polymerase. The assay was designed to measure the time between captures of tagged nucleotide molecule by a DNA polymerase attached to the nanopore using alternating voltages, i.e., squarewaves.

Sequencing template HP7, an in-house dumbbell template was used in this example.

The variant Pol6 polymerase is contacted with DNA template to form variant Pol6-DNA complex, which is subsequently attached to a nanopore embedded in a lipid bilayer over a well on a semiconductor sensor chip, also called a biochip. The lipid bilayer is formed and the nanopore with attached variant Pol6 polymerase-DNA complex, i.e., the variant Pol6 nanopore sequencing complex, is inserted as described in PCT/US2014/061853 (entitled "Methods for Forming Lipid Bilayers on Biochips" and filed 23 Oct. 2014).

Alternatively, the nanopore is embedded into the lipid bilayer, and the variant Pol6-DNA complex is attached in situ.

A mixture of tagged nucleotides was used with each nucleotide having a different tag, i.e., the four nucleotides—A, T, G and C—had different tags, in a buffer (300 mM KGlu, 3 mM MgCl$_2$. 20 mM HEPES, pH8.0), and the tagged nucleotides flowed over the nanopores at a rate of 0.834 μl/second.

An alternating current of 210 mV peak to peak is applied at 25 Hz, and capture of nucleotide tags was assessed as nucleotide bases were incorporated into the copied DNA strand by the nanopore-bound polymerase.

The time between consecutive tag captures is referred to herein as the waiting time. The waiting time includes $k_{on}$, association rate for the incoming nucleotide and $k_{displace}$, the rate of strand displacement of the downstream template. Thus, the ability of the polymerase to advance to a new nucleotide, which is dependent upon the polymerase to displace the complimentary strand, may be analyzed.

The ability of two polymerases to displace the complimentary strand on a template DNA is shown by the waiting time. D44A is a mutation of catalytic aspartate in the exonuclease domain and is the most commonly used exonuclease deficient mutation. This affects strand displacement and causes long waiting times during sequencing. Y212K (an exonuclease deficient mutation provided for herein) has improved strand displacement, resulting in a faster progression rate, and a decreased waiting time. An effective doubling of the progression rate, i.e., extension or sequencing rate, with Y212K as compared to the D44A mutation of pol6 was observed (data not shown).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING FREE TEXT

SEQ ID NO: 1 - Wild-type Pol6 (DNA polymerase [Clostridium phage phiCPV4]; GenBank: AFF127113.1)

```
  1 mdkhtqyvke hsfnydeykk anfdkiecli fdtesctnye ndntgarvyg wglgvtrnhn
 61 miygqnlnqf wevcqnifnd wyhdnkhtik itktkkqfpk rkyikfpiav hnlgwdvefl
121 kyslvengfn ydkgllktvf skqapyqtvt dveepktfhi vqnnnivygc nvymdkffev
181 enkdgsttei glcldffdsy kiitcaesqf hnyvhdvdpm fykmgeeydy dtwrspthkq
241 ttlelryqyn diymlrevie qfyidglcgg elpltgmrta ssiafnvlkk mtfgeektee
301 gyinyfeldk ktkfeflrkr iemesytggy thanhkavgk tinkigcsld inssypsqma
361 ykvfpygkpv rktwgrkpkt eknevyliev gfdfvepkhe eyaldifkig avnskalspi
421 tgavsgqeyf ctnikdgkai pvykelkdtk lttnynvvlt sveyefwikh fnfgvfkkde
481 ydcfevdnle ftglkigsil yykaekgkfk pyvdhftkmk venkklgnkp ltnqakliln
541 gaygkfgtkq nkeekdlimd kngllftfge vteyegkefy rpyasfvtay grlqlwnaii
601 yavgvenfly cdtdsiycnr evnsliedmn aigetidkti lgkwdvehvf dkfkvlgqkk
661 ymyhdckedk tdlkccglps darkiiigqg fedfylgknv egkkqrkkvi ggcllldtlf
721 tikkimf
```

SEQ ID NO: 2 - Pol6 (with His tag)

```
MHHHHHHHS  GGSDKHTQYV  KEHSFNYDEY  KKANFDKIEC  LIFDTESCTN         50
YENDNTGARV  YGWGLGVTRN  HNMIYGQNLN  QFWEVCQNIF  NDWYHDNKHT        100
IKITKTKKGF  PFRKYIKFPI  AVHNLGWDVE  FLKYSLVENG  FNYDKGLLKT        150
VFSKCAPYQT  VTDVEEPKTF  HIVQNNNIVY  GCNVYMDKFF  EVENKDGSTT        200
EIGLCLDFFD  SYKIITCAES  QFHNYVHDVD  PMFYIMGEEY  DYDTWRSPTH        250
KQTTLELRYQ  YNDIYMLREV  IEQFYIDGLC  GGELPLTGMR  TASSIAFNVL        300
KKMTFGEEKT  EEGYINYFEL  DKKTKFEFLR  KRIEMESYTG  GYTHANHKAV        350
GKTINKIGCS  LDINSSYPSQ  MAYKVFPYGK  PVRKTWGRKP  KTEKNEVYLI        400
EVGFDFVEPK  HEEYALDIFK  IGAVNSKALS  PITGAVSGQE  YFCTNIKDGK        450
AIPVYKELKD  TKLTTNYNVV  LTSVSYEFWI  KHFNFGVFKK  DEYDCFEVDN        500
LEFTGLKIGS  ILYYKAEKGK  FKPYVDHFTK  MKVENKKLGN  KPLTNQAKLI        550
LNGAYGKFGT  KQNKEEKDLI  MDKNGLLTFT  GSVTEYEGKE  FYRPYASFVT        600
AYGRLQLWNA  IIYAVGVENF  LYCDTDSIYC  NREVNSLIED  MNAIGETIDK        650
TILGKWDVEH  VFDKFKVLGQ  KKYMYHDCKE  DKTDLKCCGL  PSDARKIIIG        700
QGFDEFYLGK  NVEGKKQRKK  VIGGCLLLDT  LFTIKKIMF*                    739
```

SEQ ID NO: 3 - Pol6 with His-tag (DNA sequence)

```
ATGCATCACC ATCATCATCA CCACCACAGC GGCGGTTCCG ACAAACACAC           50
GCAGTACGTC AAAGAGCATA GCTTCAATTA TGACGAGTAT AAGAAAGCGA          100
ATTTCGACAA GATCGAGTGC CTGATCTTTG ACACCGAGAG CTGCACGAAT          150
TATGAGAACG ATAATACCGG TGCACGTGTT TACGGTTGGG GTCTTGGCGT          200
CACCCGCAAC CACAATATGA TCTACGGCCA AAATCTGAAT CAGTTTTGGG          250
AAGTATGCCA GAACATTTTC AATGATTGGT ATCACGACAA CAAACATACC          300
ATTAAGATTA CCAAGACCAA GAAAGGCTTC CCGAAACGTA ACATTAAGTT          350
GTTTCCGATT GCAGTTCACA ATTTGGGCTG GGATGTTGAA TTCCTGAAGT          400
ATAGCCTGGT GGAGAATGGT TTCAATTACG ACAAGGGTCT GCTGAAAACT          450
GTTTTTAGCA AGGGTGCGCC GTACCAAACC GTGACCGATG TTGAGGAACC          500
GAAAACGTTC CATATCGTCC AGAATAACAA CATCGTTTAT GGTTGTAACG          550
TGTATATGGA CAAATTCTTT GAGGTCGAGA ACAAAGACGG CTCTACCACC          600
GAGATTGGCC TGTGCTTGGA TTTCTTCGAT AGCTATAAGA TCATCACGTG          650
TGCTGAGAGC CAGTTCCACA ATTACGTTCA TGATGTGGAT CCAATGTTCT          700
ACAAAATGGG TGAACACTAT CATTACGATA CTTGCGGTAG CCCCACGACG          750
AAGCAGACCA CCCTCGAGCT CCGCTACCAA TACAATGATA TCTATATGCT          800
GCGTGAAGTC ATCGAACAGT TTTACATTGA CGGTTTATGT GGCGGCGAGC          850
TGCCGCTGAC CGGCATGCGC ACGCCTTCCA GCATTGCGTT CAACCTGCTG          900
AAAAAGATGA CCTTTGGTGA GGAAAAGACG GAAGAGGGCT AEATCAACTA          950
TTTTGAATTG GACAAGAAAA CCAAATTCGA GTTTCTGCGT AAGCGCATTG         1000
AAATGGAATC CTACACCCGT GGCTATACGC ACGCAAATCA CAAAGCCGTT         1050
GGTAAGAGTA TTAACAAGAT CGGTTGCTCT TTGGACATTA ACAGCTCATA         1100
CCCTTCGGAG ATGGCGTACA AGGTCTTTCC GTATGGCAAA CCGGTTCGTA         1150
AGACCTGGGG TCGTAAACCA AAGACCGAGA GAACGAAGT TTATCTGATT          1200
GAAGTTGGCT TTGACTTCGT GGAGCCGAAA CACGAAGAAT ACGCGCTGGA         1250
TATCTTTAAG ATTGGTGCGG TGAACTCTAA AGCGCTGAGC CCGATCACCG         1300
GCGCTGTCAG CGGTCAAGAG TATTTCTGTA CGAACATTAA AGACGGCAAA         1350
GCAATCCCGG TTTACAAAGA ACTGAAGGAC ACCAAATTGA CCACTAACTA         1400
CAATGTCCTG CTGACCAGCG TCGAGTACCA GTTCTGGATC AAACACTTCA         1450
ATTTTGGTGT GTTTAAGAAA GACGAGTACG ACTGTTTCGA.AGTTGACAAT         1500
CTGCACTTTA CGGGTCTGAA CATTGGTTCC ATTCTCTACT ACAAGGCAGA         1550
GALAGGCAAG TTTAAACCTT ACGTGGATCA CTTCACGAAA ATGAAAGTGG         1600
AGAACAAGAA ACTGGGTAAT AAGCCGCTGA CGAATCAGGC AAAGCTGATT         1650
CTGAACGGTG CGTACGGCAA ATTCGGCACC AAACAAAACA AAGAAGAGAA         1700
AGATTTGATC ATGGATAAGA ACGGTTTGCT GACCTTCACG GGTAGCGTCA         1750
CGGAATACGA GGGTAAAGAA TTCTATCGTC CGTATGCGAG CTTCGTTACT         1800
GCCTATGGTC GCCTGCAACT GTGGAACGCG ATTATCTACG CGGTTGGTGT         1850
GGAGAATTTT CTGTACTGCG ACACCGACAG CATCTATTGT AACCGTGAAG         1900
TTAACAGCCT CATTGAGGAT ATGAACCCCA TTGGTGAAAC CATCCATAAA         1950
ACGATTCTGG GTAAATGGGA CGTTGAGCAT GTCTTTGATA AGTTTAAGGT         2000
CCTGGGCCAA AAGAAGTACA TGTTCATGAT TTGCAAAGAA GATAAAACGG         2050
ACCTGAAGTC TTGCGGTCTG CCGACCCATG CCCCTAACAT TATCATTGGT         2100
CAAGGTTTCG ACGAGTTTTA TCTGGGCAAA AATGTCGAAG GTAAGAAGCA         2150
ACGCAAAAAA GTGATCGGCG GTTGCCTGCT GCTGGACACC CTGTTTACGA         2200
TCAAGAAAAT CATGTTCTAA                                          2220
```

-continued

SEQUENCE LISTING FREE TEXT

SEQ ID NOS 4 and 14 - Displacement Assay Hairpin Oligo with iSpC3, a
3-carbon spacer
AGA GTG ATA GTA TGA TTA TGT AGA TGT AGG ATT TGA TAT GTG AGT AGC CGA
ATG AAA CCT T/iSpC3/TT GGT TTC ATT CGG SEQ ID NO: 5 - Displacement Assay Short Oligo
TTT TCA TAA TCA TAC TAT CAC TCT SEQ ID NO: 6 - Exonuclease Assay Hairpin Oligo
AGA GTG ATA GTA TGA TTA TGT AGA TGT AGG ATT TGA TAT GTG AGT AGC CGA
ATG AAA CCT TTG GTT TCA TTC GG SEQ ID NO: 7 - Exonuclease Assay Short Oligo
TTT TCA TAT CAA ATC CTA CAT CTA CAT AAT CAT ACT ATC ACT CT SEQ ID NO: 8 - pol6 variant (T529M + S366A + A547F; no His-Tag)
  1 MDKHTQYVKE HSFNYDEYKK ANFDKIECLI FDTESCTNYE NDNTGARVYG WGLGVTRNHN
 61 MIYGQNLNQF WEVCQNIFND WYHDNKHTIK ITKTKKGFPK RKYIKFPIAV HNLGWDVEFL
121 KYSLVENGFN YDKGLLKTVF SKGAPYQTVT DVEEPKTPHI VQNNNIVYGC NVYMDKFFEV
181 ENKDGSTTEI GLCLDFFDSY KIITCAESQF HNYVHDVDPM FYKMGEEYDY DTWRSPTHKQ
241 TTLELRYQYN DIYMLREVIE QFYIDGLCGG ELPLTGMRTA SSIAFNVLKK MTFGEEKTEE
301 GYINYFELDK KTKFEFLRKR IEMESYTGGY THANHKAVGK TINKIGCSLD INSAYPSQMA
361 YKVFPYGKPV RKTWGRKPKT EKNEVYLTEV GFDFVEPKHE EYALDIFKIG AVNSKALSPI
421 TGAVSGQEYF CTNIKDGKAI PVYKELKDTK LTTNYNVVLT SVEYEFWIDH FNFGVFKKDE
481 YDCFEVDNLE FTGLKIGSIL YYKAEKCKFK PYVDHFMKMK VENKKLGNKP LTNQFKLILN
541 GAYGKFGTYQ NKEEKDLIMD KNGLLTFTGS VTEYEGKEFY RPYASFVTAY GRLQLWNAII
601 YAVGVENFLY CDTDSIYCNR EVNSLIEDMN AIGETIDKTI LGKWDVEHVF DKFKVLGQKK
661 YMYHDCKEDK TDLKCCGLPS DARKIIIGQG FDEFYLGKNV EGKKQRKKVI GGCLLLDTLF
721 TIKKIMF SEQ ID NO: 9 - HFCirc10
CGC TCA CAC TCG CTC TCT CTA CGT CAC TCA TCT CAC TAC TGC ACT CTA CTC
GAC ACT CTA CTA CAG CTA GCT CTC TCT ACG ACG CAC ATC ACG CTA CTA CAC
TCT GCT CTA CAC TAC ACT CTC TCT ACA TCG CTC TAC TAC GCT CAT CTA

SEQ ID NO: 10 - Primer for HFCirc10
GTG TGA GCG TAG ATG AGC

SEQ ID NO: 11 pol6 variant (D44A + T529M + S366A + A547F: no His-Tag)
  1 MDKHTQYVKE HSFNYDEYKK ANFDKIECLI FATESCTNYE NDNTGARVYG WGLGVTRNHN
 61 MIYGQNLNQF WEVCQNIFND WYHDNKHTIK ITKTKKGFPK RKYIKFPIAV HNLGWDVEFL
121 KYSLVENGFN YDKGLLKTVF SKGAPYQTVT DVEEPKTPHI VQNNNIVYGC NVYMDKFFEV
181 ENKDGSTTEI GLCLDFFDSY KIITCAESQF HNYVHDVDPM FYKMGEEYDY DTWRSPTHKQ
241 TTLELRYQYN DIYMLREVIE QFYIDGLCGG ELPLTGMRTA SSIAFNVLKK MTFGEEKTEE
301 GYINYFELDK KTKFEFLRKR IEMESYTGGY THANHKAVGK TINKTGCSLD INSAYPSQMA
361 YKVFPYGKPV RKTWGRKPKT EKNEVYLIEV GFDFVEPKHE EYALDIFKIG AVNSKALSPI
421 TGAVSGQEYF CTNIKDGKAI PVYKELKDTK LTTNYNVVLT SVEYFFWIKH FNFGVFKKDF
481 YDCEFVDNLE FTGLKIGSIL YYKAEKGKFK PYVDHFMKMK VENKKLGNKP LTNQFKLILN
541 GAYGKFGTKQ NKEEKDLIMD KNGLLTFTGS VTEYEGKEFY RPYASFVTAY GRLQLWNAII
601 YAVGVENFLY CDTDSIYCNR EVNSLIEDMN AIGETIDKTI LGKWDVEHVF DKFKVLGQKK
661 YMYHDCKEDK TDLKCCGLPS DARKIIIGQG FDEFYLGKNV EGKKQRKKVI GGCLLLDTLF
721 TIKKIMF

CITATION LIST

Patent Literature

[1] PCT/US2005/009702 (published as WO02006/028508 on 16 Mar. 2006; President and Fellows of Harvard College; entitled METHODS AND APPARATUS FOR CHARACTERIZING POLYNUCLEOTIDES.
[2] PCT/US2011/065640 (published as WO2012/083249 on 21 Jun. 2012; Columbia University; entitled DNA SEQUENCING BY SYNTHESIS USING MODIFIED NUCLEOTIDES AND NANOPORE DETECTION).
[3] PCT/US2013/068967 (published as WO2014/074727 on 15 May 2014; Genia Technologies; entitled NUCLEIC ACID SEQUENCING USING TAGS).
[4] PCT/US2013/046012 (Genia Technologies, Inc., entitled CHIP SET-UP AND HIGH-ACCURACY NUCLEIC ACID SEQUENCING, published 19 Dec. 2013 as WO2013/188841).
[5] US 2013/0053544 (Isis Innovation Limited) entitled Peptide Tag Systems That Spontaneously Form an Irreversible Link to Protein Partners via Isopeptide Bonds.

Non-Patent Literature

[6] Altschul, S. F., et al., 1990
[7] Altschul, S. F., et al., Nucleic Acids Res. 25:3389-3402, 1997
[8] Ausubel, Frederick at al., (1992) Short Protocols in Molecular Biology, Current Protocols in Molecular Biology, 2nd ed., Greene Publishing Associates & John Wiley & Sons. New York, N.Y.
[9] Gardner et al., Nucleic Acids Res. (2012) pages 1-12 (doi: 10.1093/nar/gks330; First published online: May 8, 2012)
[10] Hale & Martam, THE HARPER COLLINS DICTIONARY OF BIOLOGY, Harper Perennial, NY (1991)

[11] Johnson, et al., Biochim Biophys Acta. 2010 May; 1804(5): 1041-1048
[12] Kong et al. (1993) *J. Biol. Chem.* 268(3); 1965-1975)
[13] Lawyer et al. (1989) J. Biol. Chem. 264:6427-647
[14] Li et al, J Mol Biol. 2014 Jan. 23; 426(2):309-17
[15] Sambrook et al., (1989) Molecular Cloning: A Laboratory Manual (2$^{nd}$ ed., Cold Spring Harbor Laboratory Press, NY)
[16] Sambrook at al. (2001) Molecular Cloning: A Laboratory Manual (3$^{rd}$ ed., Cold Spring Harbor Laboratory Press, NY) at 9.63-9.75 (describing end-labeling of nucleic acids).
[17] Singleton, et al., DICTIONARY OF MICROBIOLOGY AND MOLECULAR BIOLOGY, 2D ED., John Wiley and Sons, New York (1994)
[18] Watson, J. D. et al., In: Molecular Biology of the Gene, 4th Ed., W. A. Benjamin, Inc., Menlo Park, Calif. (1987))
[19] Zakari and Howarth, (2010) Spontaneous Intermolecular Amide Bond Formation between Side Chains for Irreversible Peptide Targeting, J. Am. Chem. Soc., 132 (13):4526-4527
[20] Zakari, B. et al., (2012) Peptide tag forming a rapid covalent bond to a protein, through engineering a bacterial adhesion, PNAS 109 (12):E690-E697.

What is claimed is:

1. A modified DNA polymerase, derived from a parental DNA polymerase polypeptide having a DNA polymerase activity comprising an amino acid sequence having at least 80% sequence identity to the amino acid sequence as set forth in SEQ ID NO: 1, comprising a substitution at a position corresponding to a position of SEQ ID NO: 2, wherein the modified polymerase is exonuclease deficient.

2. The modified DNA polymerase according to claim 1, wherein said modified polymerase retains a strand displacement capability.

3. The modified DNA polymerase according to claim 1, wherein said modified polymerase has a substitution selected from the group consisting of Y242G, Y242A, Y242L, and Y242S.

4. The modified DNA polymerase according to claim 1, wherein said modified polymerase has at least 90%, 95%, 96%, 97%, 98% or 99% sequence identity to SEQ ID NO: 1.

5. The modified DNA polymerase according to claim 1, wherein said modified polymerase has an extension rate that is greater than the parental polymerase.

6. The modified DNA polymerase of claim 5, wherein the extension rate is between 1.5 to 5 times greater than the parental polymerase.

7. The modified DNA polymerase of claim 5, wherein the extension rate is at least 1.5 times greater than the parental polymerase.

8. The modified DNA polymerase according to claim 1, wherein said modified polymerase has a median waiting time that is less than the wild-type or parental polymerase.

9. The modified DNA polymerase according to claim 8, wherein said modified polymerase has a median waiting time that is less than the waiting time of the polymerase according to SEQ ID NO: 11.

10. The modified DNA polymerase according to claim 8, wherein said modified polymerase has a median waiting time that is less than 3 seconds.

11. The modified DNA polymerase according to claim 1, wherein said modified polymerase has a substitution corresponding to Y242G.

12. The modified DNA polymerase according to claim 1, wherein said modified polymerase has a substitution corresponding to Y242A.

13. The modified DNA polymerase according to claim 1, wherein said modified polymerase has a substitution corresponding to Y242L.

14. The modified DNA polymerase according to claim 1, wherein said modified polymerase has a substitution corresponding to Y242S.

15. The modified DNA polymerase according to claim 1, wherein said modified polymerase comprises T529M+S366A+A547F+Y242G/A/L/S.

* * * * *

UNITED STATES PATENT AND TRADEMARK OFFICE
CERTIFICATE OF CORRECTION

PATENT NO.       : 10,266,813 B2
APPLICATION NO.  : 15/444020
DATED            : April 23, 2019
INVENTOR(S)      : Aruna Ayer et al.

Page 1 of 1

It is certified that error appears in the above-identified patent and that said Letters Patent is hereby corrected as shown below:

In Claim 1, at Column 45, Line 42, the term --Y242-- should be inserted between "a position" and "of SEQ ID NO: 2."

Signed and Sealed this
Ninth Day of July, 2019

Andrei Iancu
*Director of the United States Patent and Trademark Office*